US010329630B2

(12) United States Patent
Shu et al.

(10) Patent No.: US 10,329,630 B2
(45) Date of Patent: Jun. 25, 2019

(54) COMPOSITIONS AND METHODS FOR DETECTION AND DISCRIMINATION OF EMERGING INFLUENZA VIRUS SUBTYPES

(71) Applicant: The United States of America, as represented by the Secretary, Dept. of Health and Human Services, Washington, DC (US)

(72) Inventors: Bo Shu, Lilburn, GA (US); Stephen Lindstrom, Chamblee, GA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/834,555

(22) Filed: Dec. 7, 2017

(65) Prior Publication Data

US 2018/0163277 A1 Jun. 14, 2018

Related U.S. Application Data

(60) Provisional application No. 62/432,340, filed on Dec. 9, 2016.

(51) Int. Cl.

*C12Q 1/70* (2006.01)
*C12Q 1/68* (2018.01)
*C12Q 1/682* (2018.01)
*C12Q 1/6818* (2018.01)

(52) U.S. Cl.

CPC ............. *C12Q 1/701* (2013.01); *C12Q 1/682* (2013.01); *C12Q 1/70* (2013.01); *C12N 2760/16111* (2013.01); *C12Q 1/6818* (2013.01)

(58) Field of Classification Search

None

See application file for complete search history.

(56) References Cited

U.S. PATENT DOCUMENTS

2003/0050470 A1* 3/2003 An ......................... C07H 21/00 536/24.3
2011/0236898 A1 9/2011 Rose et al.

FOREIGN PATENT DOCUMENTS

| | | | | |
|---|---|---|---|---|
| KR | 20110028188 | | 3/2011 | |
| WO | WO 2007/095155 | | 8/2007 | |
| WO | WO2007095155 | * | 8/2007 | ............... C12Q 1/68 |
| WO | WO2008042450 | * | 4/2008 | ............... C12Q 1/70 |
| WO | WO 2012/009373 | | 1/2012 | |
| WO | WO 2014/160797 | | 10/2014 | |
| WO | WO 2015/061475 | | 4/2015 | |
| WO | WO2015061475 | * | 4/2015 | ............... C12Q 1/70 |

OTHER PUBLICATIONS

Ducatez MF, Awoume F, Webby RJ. Influenza A(H1N1)pdm09 virus in pigs, Togo, 2013. Vet Microbiol. May 15, 2015; 177(1-2):201-5. Epub Mar. 4, 2015. (Year: 2015).*

Garten et al. Antigenic and genetic characteristics of swine-origin 2009 A(H1N1) influenza viruses circulating in humans. Science. Jul. 10, 2009; 325(5937):197-201. Epub May 22, 2009. (Year: 2009).*

Garten et al. Supplemental—pp. 1-28. Science Jul. 10, 2009; 325(5937):197-201. (Year: 2009).*

Genbank Accession No. CY128032—Influenza A virus (A/Viet Nam/831/2009(H1)) hemagglutinin (HA) gene, partial cds (submitted Nov. 29, 2012, retrieved on Jun. 19, 2018 from http://www.ncbi.nlm.nih.gov/nuccore/CY128032). (Year: 2012).*

Genbank Accession No. FJ969536—Influenza A virus (A/California/07/2009(H1N1)) segment 5 nucleocapsid protein (NP) gene, complete cds (submitted Apr. 28, 2009, retrieved on Jun. 19, 2018 from http://www.ncbi.nlm.nih.gov/nuccore/FJ969536). (Year: 2009).*

Genbank Accession No. FJ966974—Influenza A virus (A/California/07/2009(H1N1)) segment 4 hemagglutinin (HA) gene, complete cds (submitted Apr. 27, 2009, retrieved on Jun. 19, 2018 from http://www.ncbi.nlm.nih.gov/nuccore/FJ966974). (Year: 2009).*

Genbank Accession No. KU323245 Influenza A virus (A/swine/Italy/179057/2015(H1N1)) segment 4 hemagglutinin (HA) gene, complete cds (submitted Dec. 18, 2015, retrieved on Jun. 19, 2018 from http://www.ncbi.nlm.nih.gov/nuccore/KU323245). (Year: 2015).*

Genbank Accession No. KU323237—Influenza A virus (A/swine/Italy/161692/2015(H1N1)) segment 4 hemagglutinin (HA) gene, complete cds (submitted Dec. 18, 2015, retrieved on Jun. 19, 2018 from http://www.ncbi.nlm.nih.gov/nuccore/KU323237). (Year: 2015).*

Genbank Accession No. NM_006413—*Homo sapiens* ribonuclease P/MRP subunit p30 (RPP30), transcript variant 2, mRNA *Homo sapiens* ribonuclease P/MRP subunit p30 (RPP30), transcript variant 2, mRNA (submitted Sep. 2007, retrieved on Jun. 19, 2018 from http://www.ncbi.nlm.nih.gov/nuccore/NM_006413). (Year: 2007).*

Genbank Accession No. JF915184—Influenza A virus (A/California/04/2009(H1N1)) segment 4 hemagglutinin (HA) gene, complete cds (submitted May 4, 2011, retrieved on Jun. 20, 2018 from http://www.ncbi.nlm.nih.gov/nuccore/JF915184). (Year: 2011).*

Genbank Accession No. GQ334330—Influenza A virus (A/Fukuoka-C/2/2009(H1N1)) segment 4 hemagglutinin (HA) gene, complete cds (submitted Jun. 30, 2009, retrieved on Jun. 20, 2018 from http://www.ncbi.nlm.nih.gov/nuccore/GQ334330). (Year: 2009).*

(Continued)

*Primary Examiner* — Gary Benzion
*Assistant Examiner* — Olayinka A Oyeyemi
(74) *Attorney, Agent, or Firm* — Klarquist Sparkman, LLP

(57) ABSTRACT

Compositions and methods for detecting presence of an emerging influenza virus in a sample, such as a biological sample obtained from a subject or an environmental sample, are disclosed. In some embodiments, the compositions and methods can be used to quickly identify particular subtypes of influenza virus (such as a pandemic and/or emerging influenza virus subtype). Probes and primers are provided herein that permit the rapid detection and/or discrimination of pandemic influenza virus subtype nucleic acids in a sample. Devices (such as arrays) and kits for detection and/or discrimination of influenza virus subtype nucleic acids are also provided.

17 Claims, No Drawings

Specification includes a Sequence Listing.

(56) References Cited

OTHER PUBLICATIONS

SantaLucia Jr, John. Physical principles and visual-OMP software for optimal PCR design. PCR Primer Design. Humana Press, 2007: pp. 3-33. (Year: 2007).*
Shu et al. (2011, Supplemental, pp. 1-11, J Clin Microbiol. Jul. 2011; 49(7):2614-9). (Year: 2011).*
WHO/CDC. 2009. CDC protocol of real time RT PCR for swine influenza A (H1N1). WHO Collaborating Centre for Influenza at CDC Atlanta, United States of America, Atlanta, GA. (Year: 2009).*
Yang et al. Simultaneous typing and HA/NA subtyping of influenza A and B viruses including the pandemic influenza A/H1N1 2009 by multiplex real-time RT-PCR. J Virol Methods. Jul. 2010; 167(1):37-44. Epub Mar. 19, 2010. (Year: 2010).*
Yang Y, Huang F, Gonzalez R, Wang W, Lu G, Li Y, Vernet G, Jin Q, Wang J. Evaluation of twelve real-time reverse transcriptase PCR primer-probe sets for detection of pandemic influenza A/H1N1 2009 virus. J Clin Microbiol. Apr. 2011; 49(4):1434-40.Epub Feb. 2, 2011. (Year: 2011).*
CDC, "CDC Influenza 2009 A(H1N1)pdm Real-Time RT-PCR Panel," CDC Influenza Division, Virus Surveillance and Diagnosis Branch, Jun. 29, 2010 (50 pages).
CDC, "New CDC Test to Detect Human Infections with the 2009 H1N1 Influenza Virus Authorized for Use by FDA," CDC Newsroom: press release, Jun. 22, 2010 (1 page).
CDC, "Realtime RTPCR (rRTPCR) Protocol for Detection and Characterization of Swine Influenza (version 2009)," 8 pages, Apr. 28, 2009 (with revisions through Oct. 6, 2009).
CDC, "Seasonal Influenza Real-time rRT-PCR Panel Primer and Probe Sets," Jun. 8, 2012 (2 pages).
CDC, "Special 510(k): Device Modification OIR Decision Summary, K161556," Jun. 30, 2016 (10 pages).
Shu et al., "Design and Performance of the CDC Real-Time Reverse Transcriptase PCR Swine Flu Panel for Detection of 2009 A (H1N1) Pandemic Influenza Virus," *Journal of Clinical Microbiology*, vol. 49, No. 7, pp. 2614-2619, 2011.
Shu et al., "Design Strategy, Optimization, and Performance of the CDC Influenza 2009 A (H1N1) Pandemic (PDM) Real-Time RT-PCR Panel," *International Conference on Emerging Infectious Diseases*, Atlanta, Georgia, Jul. 11-14, 2010 (1 page).
Shu et al., "Improved Methods to Detect and Characterize the 2009 Pandemic A (H1N1) Influenza Virus Using the CDC rRT-PCR 2009 A (H1N1) pdm Flu Panel," *Options for the control of influenza VII*, Hong Kong, Sep. 3-7, 2010 (1 page).
Wu et al., "Updated CDC real-time RT-PCR Influenza Assay for Detection of Recently Circulating Human A(H1N1)pdm09 Influenza Viruses," *Sixth European Scientific Working Group on Influenza Conference*, Riga, Latvia, Sep. 10-14, 2017 (1 page).

* cited by examiner

SEQUENCE LISTING

```
<160> NUMBER OF SEQ ID NOS: 37

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1

gtgctataaa caccagcctc ccatt                                    25


<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 2

agaygggaca ttcctcaatc ctg                                      23
```

<210> SEQ ID NO 3
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 3
atacatccra tcacaattgg raaatgtcca aa 32

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
gaccratcct gtcacctctg ac 22

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 5
agggcattyt ggacaaakcg tcta 24

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6
tgcagtcctc gctcactggg cacg 24

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
ttgcagtagc aagtgggcat ga 22

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 8
tcttgtgagc tgggttttca tttg 24

<210> SEQ ID NO 9
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 9
tgaatgggtc tatcccgacc agtgagtac 29

<210> SEQ ID NO 10
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 10
gatctyaaaa gcactcargc agc 23

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 11
aggtcctgaa ttctyccttc kac 23

<210> SEQ ID NO 12
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 12
gatctyaaaa gcactcargc agctcccgat caayckattc agcttcccat tga 53

<210> SEQ ID NO 13
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 13
tcttgattac tctrttyagt ttcccggtg 29

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 14
tggaaagtgt ragaaacggr acrta 25

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 15
tggaaagtat aagraacgga acrta 25

<210> SEQ ID NO 16

<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 16
ctagggarct cgccactgtw ga 22

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
ctagdgaact cgcarctgtt ga 22

<210> SEQ ID NO 18
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 18
tgactacccg cagtattcag aagaakcaag aytaa 35

<210> SEQ ID NO 19
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 19
caactatccg cagtattcag aagaagcaag attaa 35

<210> SEQ ID NO 20
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 20
ggaatgyccc aaatatgtga aatcaa 26

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
ccrctcccct gctcrttrct 20

<210> SEQ ID NO 22
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 22
tacccatacc aaccatctac catyccctgc cat 33

<210> SEQ ID NO 23
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 23
aatgcacarg grgagggaac tgc 23

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
cattgctacy aagagttcag crtt 24

<210> SEQ ID NO 25
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 25
accacacytc tgtyatrgaa tctctggtcc a 31

<210> SEQ ID NO 26
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 26
aaaygcacaa ggagarggaa ctgc 24

<210> SEQ ID NO 27
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 27
gcattrtacg accatayctc agtcatt 27

<210> SEQ ID NO 28
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 28
aaagcacyca rtctgcaata gatcagatca cagg 34

<210> SEQ ID NO 29
<211> LENGTH: 23
<212> TYPE: DNA

<213> ORGANISM: Artificial Sequence
<220> FEATURE:
<223> OTHER INFORMATION: Synthetic oligonucleotide

<400> SEQUENCE: 29
ctggartctg arggractta caa 23

<210> SEQ ID NO 30
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 30
aaraaggcag caaaccccat tg 22

<210> SEQ ID NO 31
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 31
cyatttattc ractgtcgcc tcatctcttg 30

<210> SEQ ID NO 32
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 32
tcctcaaytc actcttcgag cg 22

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 33
cggtgctctt gaccaaattg g 21

<210> SEQ ID NO 34
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 34
ccaattcgag cagctgaaac tgcggtg 27

<210> SEQ ID NO 35
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 35
agatttggac ctgcgagcg 19

-continued

```
<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36

gagcggctgt ctccacaagt                                             20


<210> SEQ ID NO 37
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 37

tctgacctga aggctctgcg cg                                          22
```

COMPOSITIONS AND METHODS FOR DETECTION AND DISCRIMINATION OF EMERGING INFLUENZA VIRUS SUBTYPES

CROSS REFERENCE TO RELATED APPLICATIONS

This application claims the benefit of U.S. Provisional Application No. 62/432,340, filed Dec. 9, 2016, which is incorporated herein by reference in its entirety.

FIELD

This disclosure relates to probes and primers for detecting influenza virus and methods of using the probes and primers.

BACKGROUND

Influenza virus type A is a member of the orthomyxoviridae family of viruses that cause influenza infection. The infective potential of influenza is frequently underestimated and can result in high morbidity and mortality rates, especially in elderly persons and in high-risk patients, such as the very young and the immuno-compromised. Influenza A viruses primarily infect the nasopharyngeal and oropharyngeal cavities and produce highly contagious, acute respiratory disease that results in significant morbidity and economic costs. Typical influenza viral infections in humans have a relatively short incubation period of one to two days, with symptoms that last about a week including an abrupt onset of fever, sore throat, cough, headache, myalgia, and malaise. When a subject is infected with a highly virulent strain of influenza these symptoms can progress rapidly to pneumonia and in some circumstances death. Pandemic outbreaks of highly virulent influenza present a serious risk to human and animal health worldwide.

The immunodominant antigens present on the surface of influenza viruses are hemagglutinin (HA or H) and neuraminidase (NA or N). Genetic reassortment between human and avian or swine influenza viruses can result in a novel virus with a hemagglutinin and/or neuraminidase against which humans lack immunity. In the $20^{th}$ century, the pandemics of 1918, 1957, and 1968 were the result of such antigenic shifts. The avian and swine influenza outbreaks of the early $21^{st}$ century caused by 2009 pandemic influenza A(H1N1) (H1N1pdm09) subtype influenza viruses, and their infection of humans, have created a new awareness of the pandemic potential of influenza viruses that circulate in domestic poultry and swine. The impact of a major influenza pandemic has been estimated to be up as many as 200,000 deaths, 730,000 hospitalizations, 42 million outpatient visits, and 50 million additional illnesses in the U.S. alone.

Thus, the need remains for tests that provide sensitive, specific detection of influenza types and subtypes in a relatively short time in order to permit rapid and effective treatment of an infected person. In addition, detection and characterization of novel viruses infecting humans and wild or domesticated animals are critical for detection and vaccination for emerging influenza viruses, including those with pandemic potential.

SUMMARY

The present disclosure relates to compositions and methods for detecting presence of an influenza virus in a sample. The disclosed compositions and methods can be used for diagnosing an influenza infection in a subject suspected of having an influenza infection by analyzing a biological specimen from a subject to detect a variety of influenza subtypes. The compositions and methods can also be used to quickly identify particular subtypes of influenza virus (such as 2009 pandemic influenza A, 2009 pandemic influenza A subtype H1, seasonal or variant influenza subtype H3, influenza subtype H5, influenza subtype Eurasian or North American H7 and/or influenza subtype H9) present in a sample. Probes and primers are provided herein that permit the rapid detection and/or discrimination of influenza virus subtype nucleic acids in a sample.

Disclosed herein are probes capable of hybridizing to and discriminating influenza viruses from specific subtypes. In some embodiments, the probes are between 20 and 40 nucleotides in length and are capable of hybridizing to an influenza HA nucleic acid in a subtype-specific manner. In several embodiments, the probes are between 20 and 40 nucleotides in length and include a nucleic acid sequence at least 90% identical to the nucleic acid sequence of SEQ ID NO: 3, or the reverse complement thereof. In some examples, the probe is labeled with a detectable label (such as a fluorophore and/or fluorescent quencher) (for example the detectable label can be attached to the probe).

Also disclosed herein are primers capable of hybridizing to and directing amplification of an influenza nucleic acid, such as an influenza HA nucleic acid, in a subtype-specific manner. In some embodiments, the primers are between 20 and 40 nucleotides in length and include a nucleic acid sequence at least 90% identical to the nucleic acid sequence of SEQ ID NO: 1 or SEQ ID NO: 2 or the reverse complement thereof.

Disclosed herein are methods of detecting influenza virus nucleic acid and/or discriminating the subtype of an influenza virus nucleic acid in a sample (such as a biological sample from a subject or an environmental sample). In some embodiments, the methods include contacting a sample with one or more of the probes disclosed herein and detecting hybridization between the sample and an influenza virus nucleic acid in the sample. In some examples, detecting hybridization between the sample and the probe indicates presence of an influenza virus nucleic acid in the sample and/or an influenza virus infection in a subject.

In some embodiments, the disclosed methods permit detecting or discriminating presence of influenza A subtype H1, such as a subtype H1 pandemic 2009 virus, in the sample. In some examples, the sample is contacted with a nucleic acid probe including or consisting of the sequence of SEQ ID NO: 3. In some examples, detecting hybridization of the probe of SEQ ID NO: 3 to an influenza virus nucleic acid in the sample indicates the presence of influenza subtype H1 pandemic 2009 virus nucleic acid in the sample. In some examples, the sample is further contacted with a nucleic acid probe including or consisting of the sequence of SEQ ID NO: 6. In some samples, detecting hybridization of the probe of SEQ ID NO: 6 to an influenza virus nucleic acid in the sample indicates the presence of influenza type A in the sample. In some examples, the sample is further contacted with a nucleic acid probe including or consisting of the sequence of SEQ ID NO: 9. In some samples, detecting hybridization of the probe of SEQ ID NO: 9 to an influenza virus nucleic acid in the sample indicates the presence of influenza type A pandemic 2009 in the sample.

In some embodiments, the methods further include amplifying the influenza virus nucleic acid with at least one primer capable of hybridizing to and amplifying the influenza virus nucleic acid. In some embodiments, the methods further include contacting the sample with one or more of the primers disclosed herein (such as one or more pairs of primers disclosed herein) and amplifying the influenza virus nucleic acid.

In some examples, the methods include contacting the sample with one or more influenza subtype H1 pandemic 2009 primers (for example, one or more primers of SEQ ID NO: 1 or SEQ ID NO: 2). In some examples, the methods of detecting influenza subtype H1 pandemic 2009 virus further include contacting the sample with one or more influenza type A primers (for example, one or more primers of SEQ ID NO: 4 or SEQ ID NO: 5). In some examples, the methods of detecting influenza subtype H1 pandemic 2009 virus further include contacting the sample with one or more influenza type A pandemic 2009 primers (for example, one or more primers of SEQ ID NO: 7 or SEQ ID NO: 8). In additional examples, the methods further include contacting the sample with one or more influenza type and subtype probes and one or more influenza type or subtype primers useful for the detection of influenza type B, influenza subtypes H1, H3 (seasonal and/or variant), H5, H7 (subtype Eurasian and/or North American), and/or H9 (e.g., see Table 1).

The disclosure also includes methods of diagnosing an influenza infection in a subject suspected of having an influenza infection, such as an influenza H1 pandemic 2009 virus infection, when hybridization between the influenza virus nucleic acid and probe (as set forth in SEQ ID NO: 3) and/or one or more primers (as set forth in SEQ ID NOs: 1 or 2) is detected.

The disclosure also includes devices (such as arrays) and kits for detecting and/or discriminating an influenza nucleic acid in a sample. In some embodiments, the devices, arrays and kits include at least one of the probes disclosed herein, for example, at least one probe including a nucleic acid sequence at least 90% identical to the nucleic acid sequence of SEQ ID NO: 3, and in some examples additionally at least one probe including a nucleic acid sequence at least 90% identical to the nucleic acid sequence of SEQ ID NO: 6, SEQ ID NO: 9 SEQ ID NO: 12, SEQ ID NO: 13, SEQ ID NO: 18, SEQ ID NO: 19, SEQ ID NO: 22, SEQ ID NO: 25, SEQ ID NO: 28, SEQ ID NO: 31, and SEQ ID NO: 34. In some examples, the disclosed kits also include one or more of the primers (such as one or more pair of primers) disclosed herein, such as one or more primers including a nucleic acid sequence at least 90% identical to the nucleic acid sequence of SEQ ID NO: 1 and/or SEQ ID NO: 2, and in some examples additionally at least one primer including a nucleic acid sequence at least 90% identical to the nucleic acid sequence of SEQ ID NO: 4, SEQ ID NO: 5, SEQ ID NO: 7, SEQ ID NO: 8, SEQ ID NO: 10, SEQ ID NO: 11, SEQ ID NO: 14, SEQ ID NO: 15, SEQ ID NO: 16, SEQ ID NO: 17, SEQ ID NO: 20, SEQ ID NO: 21, SEQ ID NO: 23, SEQ ID NO: 24, SEQ ID NO: 26, SEQ ID NO: 27, SEQ ID NO: 29, SEQ ID NO: 30, SEQ ID NO: 32, or SEQ ID NO: 33. The disclosed devices, arrays, and kits may further include one or more additional probes and/or primers for typing and/or subtyping an influenza virus nucleic acid, such as one or more probes and/or primers specific for influenza type B, influenza subtype H1, influenza subtype pandemic H1, influenza subtype H3, influenza subtype H5, influenza subtype North American H7, influenza subtype Eurasian H7, or influenza subtype H9.

The foregoing and other features of the disclosure will become more apparent from the following detailed description.

SEQUENCE LISTING

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Dec. 6, 2017, and is 7748 bytes, which is incorporated by reference herein.

SEQ ID NOs: 1 and 2 are nucleic acid sequences of influenza subtype H1 pandemic 2009 forward and reverse primers, respectively.

SEQ ID NO: 3 is the nucleic acid sequence of an influenza subtype H1 pandemic 2009 probe.

SEQ ID NOs: 4 and 5 are the nucleic acid sequences of an influenza type A virus forward and reverse primers, respectively.

SEQ ID NO: 6 is the nucleic acid sequence of influenza type A probe.

SEQ ID NOs: 7 and 8 are the nucleic acid sequences of influenza type A pandemic 2009 forward and reverse primers, respectively.

SEQ ID NO: 9 is the nucleic acid sequence of influenza type A pandemic 2009 probe.

SEQ ID NOs: 10 and 11 are nucleic acid sequences of influenza subtype H3 forward and reverse primers, respectively.

SEQ ID NO: 12 is the nucleic acid sequence of an influenza subtype seasonal H3 probe.

SEQ ID NO: 13 is the nucleic acid sequence of an influenza subtype variant H3 probe.

SEQ ID NOs: 14 and 15 are the nucleic acid sequences of two influenza subtype H5 assay A (H5a) forward primers.

SEQ ID NOs: 16 and 17 are the nucleic acid sequences of two influenza subtype H5 assay A (H5a) reverse primers.

SEQ ID NOs: 18 and 19 are the nucleic acid sequences of two influenza subtype H5 assay A (H5a) probes.

SEQ ID NOs: 20 and 21 are the nucleic acid sequences of influenza subtype H5 assay B (H5b) forward and reverse primers, respectively.

SEQ ID NO: 22 is the nucleic acid sequence of an influenza subtype H5 assay B (H5b) probe.

SEQ ID NOs: 23 and 24 are nucleic acid sequences of influenza subtype Eurasian H7 forward and reverse primers, respectively.

SEQ ID NO: 25 is the nucleic acid sequence of an influenza subtype Eurasian H7 probe.

SEQ ID NOs: 26 and 27 are nucleic acid sequences of influenza subtype North American H7 forward and reverse primers, respectively.

SEQ ID NO: 28 is the nucleic acid sequence of an influenza subtype North American H7 probe.

SEQ ID NOs: 29 and 30 are nucleic acid sequences of influenza subtype H9 forward and reverse primers, respectively.

SEQ ID NO: 31 is the nucleic acid sequence of an influenza subtype H9 probe.

SEQ ID NOs: 32 and 33 are nucleic acid sequences of influenza type B forward and reverse primers, respectively.

SEQ ID NO: 34 is the nucleic acid sequence of an influenza type B probe.

SEQ ID NOs: 35 and 36 are nucleic acid sequences of human RNase P forward and reverse primers, respectively.

SEQ ID NO: 37 is the nucleic acid sequence of a human RNase P probe.

DETAILED DESCRIPTION

Since the emergence of the influenza pandemic of 2009, the 2009 A (H1N1) pandemic influenza virus has been circulating seasonally in humans worldwide. In order to facilitate surveillance of this virus and improve the control and treatment of infected patients, the CDC Influenza 2009 A (H1N1) pandemic real-time RT-PCR Panel was approved by the FDA as a domestic human diagnostic testing procedure in 2010. The panel has been manufactured as part of CDC Human Influenza Virus Real-Time RT-PCR Diagnostic Panel for detection and characterization of 2009 A (H1N1) Pandemic influenza virus. However, the CDC Influenza Division has received reports of aberrant reactivity of the pdm H1 assay caused by sporadic nucleotide substitutions in the HA gene within a small proportion of currently circulating 2009 A (H1N1) pandemic influenza viruses. Thus the influenza subtype H1 pandemic 2009 virus assay disclosed herein has been updated and optimized for sensitive and specific detection and characterization of influenza subtype H1 pandemic 2009 viruses.

I. Abbreviations

FAM 6-carboxyfluorescein

FRET fluorescence resonance energy transfer

HA hemagglutinin gene or protein

LOD limit of detection

M matrix gene or protein

NA neuraminidase gene or protein

NP nucleoprotein gene or protein

PCR polymerase chain reaction

RT-PCR reverse transcription-polymerase chain reaction rRT-PCR real-time reverse transcription-polymerase chain reaction

II. Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "a probe" includes single or plural probes and can be considered equivalent to the phrase "at least one probe." As used herein, the term "comprises" means "includes." Thus, "comprising a probe" means "including a probe" without excluding other elements. It is further to be understood that all base sizes or amino acid sizes, and all molecular weight or molecular mass values, given for nucleic acids or polypeptides are approximate, and are provided for descriptive purposes, unless otherwise indicated.

All publications, patent applications, patents, and other references mentioned herein (including GenBank® Accession numbers available as of Dec. 9, 2016) are incorporated by reference in their entirety. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the disclosure, the following explanations of terms are provided:

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated.

Other examples of in vitro amplification techniques include quantitative real-time PCR; reverse transcriptase PCR; real-time reverse transcriptase PCR (rt RT-PCR or rRT-PCR); nested PCR; strand displacement amplification (see U.S. Pat. No. 5,744,311); transcription-free isothermal amplification (see U.S. Pat. No. 6,033,881), repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134); amongst others.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Detect: To determine if an agent (such as a signal or particular nucleotide(s) or amino acid(s)) is present or absent. In some examples, this can further include quantification. Use of the disclosed probes in particular examples permits detection of a label, such as a fluorophore, for example detection of a signal from an acceptor fluorophore, which can be used to determine if an influenza virus is present.

Fluorophore: A chemical compound, which when excited by exposure to a particular stimulus such as a defined wavelength of light, emits light (fluoresces), for example at a different wavelength (such as a longer wavelength of light). Examples of particular fluorophores that can be used in the probes are disclosed herein.

"Acceptor fluorophores" are fluorophores which absorb energy from a donor fluorophore, for example in the range of about 400 to 900 nm (such as in the range of about 500 to 800 nm). Acceptor fluorophores generally absorb light at a wavelength that is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum which overlaps with the emission of the donor fluorophore, such that energy emitted by the donor can excite the acceptor. Ideally, an acceptor fluorophore is capable of being attached to a nucleic acid molecule.

"Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Fluorescence Resonance Energy Transfer (FRET): A spectroscopic process by which energy is passed between an initially excited donor to an acceptor molecule, usually separated by about 10-100 Å. The donor molecules typically emit at shorter wavelengths that overlap with the absorption of the acceptor molecule. In applications using FRET, the donor and acceptor dyes are different, in which case FRET can be detected either by the appearance of sensitized fluorescence of the acceptor or by quenching of donor fluorescence. For example, if the donor's fluorescence is quenched it indicates the donor and acceptor molecules are within the Förster radius (the distance where FRET has 50% efficiency, about 20-60 Å), whereas if the donor fluoresces at its characteristic wavelength, it denotes that the distance between the donor and acceptor molecules has increased beyond the Förster radius, such as when a TAQMAN® probe is degraded by Taq polymerase following hybridization of the probe to a target nucleic acid sequence or when a hairpin probe is hybridized to a target nucleic acid sequence. In another example, energy is transferred via FRET between two different fluorophores such that the acceptor molecule can emit light at its characteristic wavelength, which is always longer than the emission wavelength of the donor molecule.

Examples of oligonucleotides using FRET that can be used to detect amplicons include linear oligoprobes (such as HybProbes), 5' nuclease (or hydrolysis) oligoprobes (such as TAQMAN® probes), hairpin oligoprobes (such as molecular beacons, scorpion primers, UniPrimers, and sunrise primers), and minor groove binding probes.

Hybridization: The ability of complementary single-stranded DNA or RNA to form a duplex molecule (also referred to as a hybridization complex). Nucleic acid hybridization techniques can be used to form hybridization complexes between a probe or primer and a nucleic acid molecule, such as an influenza nucleic acid molecule. For example, a probe or primer having sufficient identity to an influenza nucleic acid molecule will form a hybridization complex with an influenza nucleic acid molecule.

Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (Detects Sequences that Share at Least 80% Identity)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (Detects Sequences that Share at Least 50% Identity)

Hybridization: 6×SSC at RT to 55° C. for 16-20 hours

Wash at least twice: 2×-3×SSC at RT to 55° C. for 20-30 minutes each

The probes and primers disclosed herein are capable of hybridizing to influenza nucleic acid molecules under low stringency, high stringency, and very high stringency conditions.

Influenza Virus: Influenza viruses are enveloped negative-strand RNA viruses belonging to the orthomyxoviridae family. Influenza viruses are classified on the basis of their core proteins into three distinct types: A, B, and C. Within these broad classifications, subtypes are further divided based on the characterization of two antigenic surface proteins hemagglutinin (HA or H) and neuraminidase (NA or N). While B and C type influenza viruses are largely restricted to humans, influenza A viruses are pathogens of a wide variety of species including humans, non-human mammals, and birds. Periodically, non-human strains, particularly of swine and avian influenza, have infected human populations, in some cases causing severe disease with high mortality. Reassortment between such swine or avian strains and human strains in co-infected individuals has given rise to reassortant influenza viruses to which immunity is lacking in the human population, resulting in influenza pandemics. Four such pandemics occurred during the past century (pandemics of 1918, 1957, 1968, and 2009) and resulted in numerous deaths world-wide.

Influenza viruses have a segmented single-stranded (negative or antisense) genome. The influenza virion consists of an internal ribonucleoprotein core containing the single-stranded RNA genome and an outer lipoprotein envelope lined by a matrix protein. The segmented genome of influenza consists of eight linear RNA molecules that encode ten polypeptides. Two of the polypeptides, HA and NA, include the primary antigenic determinants or epitopes required for a protective immune response against influenza. Based on the antigenic characteristics of the HA and NA proteins, influenza strains are classified into subtypes. For example, recent outbreaks of avian influenza in Asia have been categorized as H1N1, H5N1, H7N3, H7N9, and H9N2 based on their HA and NA phenotypes.

HA is a surface glycoprotein which projects from the lipoprotein envelope and mediates attachment to and entry into cells. The HA protein is approximately 566 amino acids in length, and is encoded by an approximately 1780 base polynucleotide sequence of segment 4 of the genome. Nucleotide and amino acid sequences of HA (and other influenza antigens) isolated from recent, as well as historic, avian influenza strains can be found, for example in the GenBank® database (available on the world wide web at ncbi[dot]nlm[dot]nih[dot]gov/entrez) or the Influenza Research Database (available on the world wide web at fludb[dot]org). For example, influenza H1 subtype HA sequences include GenBank® Accession Nos. AY038014, J02144, JF915184 and GQ334330; H3 subtype HA sequences include GenBank® Accession Nos. AY531037, M29257, and U97740; H5 subtype HA sequences include GenBank® Accession Nos. AY075033, AY075030, AY818135, AF046097, AF046096, and AF046088; H7 subtype HA sequences include GenBank® Accession Nos. AJ704813, AJ704812, and Z47199; H9 subtype HA sequences include GenBank® Accession Nos. AY862606, AY743216, and AY664675; and subtype H1 pandemic 2009 HA sequences include GenBank® Accession No. FJ966974; influenza type A sequences of the M gene include GenBank® Accession No. FJ966975; influenza type A pandemic 2009 sequences include GenBank® Accession No. FJ969536, all of which are incorporated by reference herein as present in the GenBank® database on Dec. 9, 2016. One of ordinary skill in the art can identify additional HA nucleic acid sequences, including those now known or identified in the future.

In addition to the HA antigen, which is the predominant target of neutralizing antibodies against influenza, the neuraminidase (NA) envelope glycoprotein is also a target of the protective immune response against influenza. NA is an approximately 450 amino acid protein encoded by an approximately 1410 nucleotide sequence of influenza genome segment 6. Recent pathogenic avian strains of influenza have belonged to the N1, N2, N3, and N9 subtypes. Exemplary NA nucleotides include for example, N1: GenBank® Accession Nos. AY651442, AY651447, and AY651483; N7: GenBank® Accession Nos. AY340077, AY340078 and AY340079; N2: GenBank® Accession Nos. AY664713, AF508892, and AF508588; N3: GenBank® Accession Nos. CY035841, CY125730, and JQ906581; and N9: GenBank® Accession Nos. KC853765, KF239720, and CY147190; all of which are incorporated by reference herein as present in the GenBank® database on Dec. 9, 2016. One of ordinary skill in the art can identify additional NA nucleic acid sequences, including those now known or identified in the future.

Isolated: An "isolated" biological component (such as an influenza nucleic acid molecule, influenza virus or other biological component) has been substantially separated or purified away from other biological components in which the component naturally occurs, such as other chromosomal and extrachromosomal DNA, RNA, and proteins. Nucleic acid molecules that have been "isolated" include nucleic acid molecules purified by standard purification methods. The term also embraces nucleic acid molecules prepared by recombinant expression in a host cell as well as chemically synthesized nucleic acid molecules, such as probes and primers. Isolated does not require absolute purity, and can include nucleic acid molecules that are at least 50% isolated, such as at least 75%, 80%, 90%, 95%, 98%, 99% or even 100% isolated.

Label or Detectable Label: An agent capable of detection, for example by spectrophotometry, flow cytometry, or microscopy. For example, a label can be attached to a nucleotide (such as a nucleotide that is part of a probe), thereby permitting detection of the nucleotide, such as detection of the nucleic acid molecule of which the nucleotide is a part. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Limit of detection (LOD): The lowest analyte concentration that can be reliably (for example, reproducibly) detected for a given type of sample and/or assay method. In some examples, LOD is determined by testing serial dilutions of a sample known to contain the analyte and determining the lowest dilution at which detection occurs. In some examples, the LOD for an influenza virus assay (such as those described herein) is expressed as level of infectivity (for example, 50% tissue culture infective dose/ml ($TCID_{50}$/ml) or 50% embryo (or egg) infective dose/ml ($EID_{50}$/ml), expressed as a login scale) or RNA copy number/μl that can be detected. One of ordinary skill in the art can determine the LOD for a particular assay and/or sample type using conventional methods.

Primers: Short nucleic acid molecules, such as a DNA oligonucleotide, for example sequences of at least 15 nucleotides, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule (such as a portion of an influenza nucleic acid), wherein the sequence of the primer is specific for the target nucleic acid molecule, for example so that the primer will hybridize to the target nucleic acid molecule under high or very high stringency hybridization conditions.

In particular examples, a primer is at least 15 nucleotides in length, such as at least 15 contiguous nucleotides complementary to a target nucleic acid molecule. Particular lengths of primers that can be used to practice the methods of the present disclosure (for example, to amplify a region of an influenza nucleic acid) include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 15-60 nucleotides, 15-50 nucleotides, 20-40 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer3 (world wide web at flypush[dot]imgen[dot]bcm[dot]tmc[dot]edu/primer/primer3_www[dot]cgi).

Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences. In one example, a primer includes a label.

Probe: An isolated nucleic acid capable of hybridizing to a target nucleic acid (such as an influenza nucleic acid), which includes a detectable label or reporter molecule attached thereto. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In a particular example, a probe includes (e.g., has attached thereto) at least one fluorophore, such as an acceptor fluorophore or donor fluorophore (or both). For example, a fluorophore can be attached at the 5'- or 3'-end of the probe. In specific examples, the fluorophore is attached to the nucleotide at the 5'-end of the probe, the nucleotide at its 3'-end, the phosphate group at its 5'-end or a modified nucleotide, such as a T internal to the probe.

Probes are generally at least 20 nucleotides in length, such as at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, or more contiguous nucleotides complementary to the target nucleic acid molecule, such as 20-60 nucleotides, 20-50 nucleotides, 20-40 nucleotides, or 20-30 nucleotides.

Quantitating a nucleic acid molecule: Determining or measuring a quantity (such as an absolute or a relative quantity) of nucleic acid molecules present, such as the number of amplicons or the number of nucleic acid molecules present in a sample. In particular examples, it is determining the relative amount or actual number of nucleic acid molecules present in a sample.

Quenching of fluorescence: A reduction of fluorescence. For example, quenching of a fluorophore's fluorescence occurs when a quencher molecule (such as the fluorescence quenchers disclosed herein) is present in sufficient proximity to the fluorophore that it reduces the fluorescence signal (for example, prior to the binding of a probe to an influenza nucleic acid sequence, when the probe contains a fluorophore and a quencher).

Real-time PCR: A method for detecting and measuring products generated during each cycle of a PCR, which are proportionate to the amount of template nucleic acid prior to the start of PCR. The information obtained, such as an amplification curve, can be used to determine the presence of a target nucleic acid (such as an influenza nucleic acid) and/or quantitate the initial amounts of a target nucleic acid sequence. In some examples, real-time PCR is real-time reverse transcriptase PCR (rRT-PCR).

In some examples, the amount of amplified target nucleic acid (such as an influenza nucleic acid) is detected using a labeled probe, such as a probe labeled with a fluorophore, for example a TAQMAN® probe. In this example, the increase in fluorescence emission is measured in real time, during the course of the RT-PCR. This increase in fluorescence emission is directly related to the increase in target nucleic acid amplification (such as influenza nucleic acid amplification). In some examples, the change in fluorescence (dRn) is calculated using the equation $dRn=Rn^+-Rn^-$, with $Rn^+$ being the fluorescence emission of the product at each time point and $Rn^-$ being the fluorescence emission of the baseline. The dRn values are plotted against cycle number, resulting in amplification plots. The threshold value (Ct) is the PCR cycle number at which the fluorescence emission (dRn) exceeds a chosen threshold, which is typically 10 times the standard deviation of the baseline (this threshold level can, however, be changed if desired).

Sample: As used herein, a sample (for example a biological sample or environmental sample) includes all types of samples useful for detecting influenza virus in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin, and/or embedded in paraffin; autopsy material; tears; milk; skin scrapes; surface washings; urine; sputum; cerebrospinal fluid; prostate fluid; pus; bone marrow aspirates; middle ear fluids; tracheal aspirates (TA); nasopharyngeal aspirates (NA) or swabs (NPS); nasal swabs (NS); nasal washes (NW); throat swabs (TS); dual nasopharyngeal/throat swabs (NPS/TS); lower respirator tract specimens (including bronchoalveolar lavage (BAL); bronchial wash (BW); sputum; lung tissue); oropharyngeal (OP) aspirates or swabs; or saliva, including specimens from human patients with signs and symptoms of respiratory infection and/or from viral culture. Samples also include environmental samples, for example, food, water (such as water from cooling towers, central air conditioning systems, swimming pools, domestic water systems, fountains, or freshwater creeks or ponds), surface swabs (for example, a swab of a counter, bed, floor, wall, or other surface), or other materials that may contain or be contaminated with influenza virus.

Sensitivity and specificity: Statistical measurements of the performance of a binary classification test. Sensitivity measures the proportion of actual positives which are correctly identified (e.g., the percentage of samples that are identified as including nucleic acid from a particular organism). Specificity measures the proportion of negatives which are correctly identified (e.g., the percentage of samples that are identified as not including nucleic acid from a particular organism).

Sequence identity/similarity: Sequence identity between two or more nucleic acid or amino acid sequences can be measured in terms of percentage identity; the higher the percentage, the more identical the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nucl. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

One indication that two nucleic acid molecules are closely related is that the two molecules hybridize to each other under stringent conditions. Stringent conditions are sequence-dependent and are different under different environmental parameters.

The nucleic acid probes and primers disclosed herein are not limited to the exact sequences shown, as those skilled in the art will appreciate that changes can be made to a sequence, and not substantially affect the ability of the probe or primer to function as desired. For example, sequences having at least 80%, at least 90%, at least 95%, at least 96%, at least 97%, at least 98%, or at least 99% sequence identity to any of SEQ ID NOS: 1-37 are provided herein. One of ordinary skill in the art will appreciate that these sequence identity ranges are provided for guidance only; it is possible that probes and primer can be used that fall outside these ranges.

Signal: A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

Subject: A living multi-cellular vertebrate organism, a category that includes human and non-human mammals and birds.

TAQMAN® probes: A linear oligonucleotide probe with a 5' reporter fluorophore (for example, 6-carboxyfluorescein (FAM)) and an internal or 3' quencher fluorophore, (for example, BLACK HOLE QUENCHER® 1 (BHQ® 1), Iowa Black® FQ quencher, and ZEN™ internal quencher). In the intact TAQMAN® probe, energy is transferred (via FRET) from the short-wavelength fluorophore to the long-wavelength fluorophore, quenching the short-wavelength fluorescence. After hybridization, the probe is susceptible to degradation by the endonuclease activity of a processing Taq polymerase. Upon degradation, FRET is interrupted, increasing the fluorescence from the short-wavelength fluorophore and decreasing fluorescence from the long-wavelength fluorophore.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule, which can include RNA (such as viral RNA) or DNA (such as DNA produced by reverse transcription of viral RNA). Purification or isolation of the target nucleic acid molecule, if needed, can be conducted by methods known to those in the art, such as by using a commercially available purification kit or the like. In one example, a target nucleic molecule is an influenza nucleic acid molecule.

III. Probes and Primers

Probes and primers capable of hybridizing to influenza virus nucleic acid molecules and suitable for use in the disclosed methods are described herein.

A. Influenza Subtype-Specific Probes

Probes capable of hybridizing to and detecting the presence of influenza nucleic acids are disclosed. The disclosed probes are between 20 and 40 nucleotides in length, such as 20, 21, 22, 23, 24, 25, 26, 27, 28, 29, 30, 31, 32, 32, 34, 35, 36, 37, 38, 39, or 40 nucleotides in length and are capable of hybridizing to influenza virus nucleic acids. In several embodiments, a probe is capable of hybridizing under high stringency or very high stringency conditions to an influenza virus nucleic acid molecule, such as an HA nucleic acid, for example an influenza subtype H1, such as a subtype H1 pandemic 2009 nucleic acid (for example, the probe of SEQ ID NO: 3). In some embodiments, a probe is capable of hybridizing under high stringency or very high stringency conditions to an influenza type A M gene nucleic acid molecule (for example, the probe of SEQ ID NO: 6). In some embodiments, a probe is capable of hybridizing under high stringency or very high stringency conditions to a pandemic influenza type A virus nucleic acid such as to an influenza type A NP gene nucleic acid (for example, the probe of SEQ ID NO: 9).

Additional probes capable of hybridizing under high stringency or very high stringency conditions to an influenza virus nucleic acid such as an HA nucleic acid, for example to influenza H1, H3, H5, H7, or H9 are provided in PCT/US2007/003646 and PCT/US2014/061802 (both incorporated by reference in their entireties) as well as Table 1. Such probes can be used in combination with the probes and primers provided herein (e.g., with the disclosed methods, devices, and kits).

In some embodiments, a probe capable of hybridizing to an influenza nucleic acid molecule includes a nucleic acid sequence that is at least 90% identical, such as at least 91%, at least 92%, at least 93%, at least 94%, at least 95%, at least 96%, at least 97%, at least 98%, at least 99%, or even 100% identical to the nucleotide sequence of SEQ ID NO: 3, SEQ ID NO: 6, SEQ ID NO: 9, SEQ ID NO: 12, SEQ ID NO: 13, SEQ ID NO: 18, SEQ ID NO: 19, SEQ ID NO: 22, SEQ ID NO: 25, SEQ ID NO: 28, SEQ ID NO: 31 or SEQ ID NO: 34. In some embodiments, a probe capable of hybridizing to an influenza nucleic acid molecule consists of or consists essentially of a nucleic acid sequence of SEQ ID NO: 3, SEQ ID NO: 6, SEQ ID NO: 9, SEQ ID NO: 12, SEQ ID NO: 13, SEQ ID NO: 18, SEQ ID NO: 19, SEQ ID NO: 22, SEQ ID NO: 25, SEQ ID NO: 28, SEQ ID NO: 31, or SEQ ID NO: 34.

In some embodiments, the probe is influenza type or subtype-specific. An influenza type-specific probe is capable of hybridizing under stringent conditions (such as high stringency or very high stringency conditions) to an influenza virus nucleic acid from a specific influenza type, such as an influenza A nucleic acid molecule or a 2009 pandemic influenza A nucleic acid molecule. An influenza subtype-specific probe is capable of hybridizing under stringent conditions (such as high stringency or very high stringency conditions) to an influenza virus nucleic acid from a specific influenza subtype, such as an influenza subtype H1 pandemic 2009. Additional subtype-specific probes are capable of hybridizing under stringent conditions (such as high stringency or very high stringency conditions) to an influenza virus nucleic acid from a specific influenza subtype, such as an influenza subtype H1, H3 (seasonal or variant), H5, H7 (Eurasian or North American), or H9. Subtype-specific probes can be used to detect the presence of and/or differentiate between various influenza subtypes. Such probes are specific for one influenza subtype, for example specific for an influenza HA nucleic acid that is subtype-specific, such as an influenza subtype H1 pandemic 2009.

In some examples, a probe that is subtype-specific for (for example, hybridizes to) influenza subtype H1 pandemic 2009 is not subtype-specific for (for example, does not substantially hybridize to) human seasonal H1 subtype, seasonal or variant influenza H3 subtype, H5 subtype, influenza H7 subtype (Eurasian or North American), or influenza H9 subtype.

In some embodiments, the probe is specific for the HA region of an influenza A nucleic acid. In a specific example, a probe specific for an influenza subtype H1 pandemic 2009 nucleic acid includes a nucleic acid sequence at least 90% identical (such as a nucleic acid sequence at least 91%, 92%, 93%, 94%, 95%, 96%, 97%, 98%, 99%, or even 100% identical) to SEQ ID NO: 3.

In certain embodiments the probes are included in a set of probes, such as one or more (for example, 1-30, 5-20, or 10-30, such as 2, 3, 4, 5, 6, 7, 8, 9, 10, 11, or 12) probes capable of hybridizing to an influenza nucleic acid molecule. In some examples, the set of probes includes a probe that is specific for influenza subtype H1 pandemic 2009 (e.g., SEQ ID NO: 3), and one or more other probes, such as probes specific for influenza type A (e.g., SEQ ID NO: 6), and/or influenza type A pandemic 2009 (e.g., SEQ ID NO: 9). Further, the probe sets can include probes for influenza B, influenza subtype seasonal H3, subtype variant H3, subtype H5, subtype Eurasian H7, subtype North American H7, and/or subtype H9, or two or more thereof (such as 2, 3, 4, 5, 6, 7, 8, or 9 of such probes) (see for example SEQ ID NO: 12, SEQ ID NO: 13, SEQ ID NO: 18, SEQ ID NO: 19, SEQ ID NO: 22, SEQ ID NO: 25, SEQ ID NO: 28, SEQ ID NO: 31, and SEQ ID NO: 34). In some embodiments, the set of probes further includes one or more control probes, such as a probe specific for a human nucleic acid (for example, RNase P, such as SEQ ID NO: 37).

The probe can be detectably labeled (e.g., have a label attached thereto), either with an isotopic or non-isotopic label, or alternatively the target nucleic acid (such as an influenza nucleic acid) is labeled. Non-isotopic labels can, for instance, include a fluorescent or luminescent molecule, a hapten (for example, biotin), an enzyme or enzyme substrate, or a chemical. Such labels are chosen such that the hybridization of the probe with target nucleic acid (such as an influenza nucleic acid) can be detected. In some examples, the probe is labeled with a fluorophore. Examples of suitable fluorophore labels are given below. In some examples, the fluorophore is a donor fluorophore. In other examples, the fluorophore is an acceptor fluorophore, such as a fluorescence quencher. In some examples, the probe includes both a donor fluorophore and an acceptor fluorophore. Appropriate donor/acceptor fluorophore pairs can be selected. In one example, the donor emission wavelength is one that can significantly excite the acceptor, thereby generating a detectable emission from the acceptor. In some examples, the probe is modified at the 3'-end to prevent extension of the probe by a polymerase.

In particular examples, the acceptor fluorophore (such as a fluorescence quencher) is attached to the 3' end of the probe and the donor fluorophore is attached to a 5' end of the probe. In another particular example, the acceptor fluorophore (such as a fluorescence quencher) is attached to a modified nucleotide (such as a T, for example, an internal T) and the donor fluorophore is attached to a 5' end of the probe. In a particular example, an acceptor fluorophore is a dark quencher, such as Dabcyl, QSY7 (Molecular Probes), QSY33 (Molecular Probes), BLACK HOLE QUENCHERS® (Glen Research, Sterling, Va., USA), ECLIPSE™ Dark Quencher (Glen Research), or IOWA BLACK® FQ (Integrated DNA Technologies, Inc., Coralville, Iowa, USA). In another particular example, the acceptor fluorophore (such as a fluorescence quencher) is an internally positioned ZEN™ quencher (Integrated DNA Technologies), and is typically located nine nucleotides from the 5' FAM reporter dye. In another particular example of the use of a ZEN™ internal quencher, an Iowa Black® FQ quencher (IABkFQ) is attached to the 3' end of the probe.

Additional exemplary fluorophores that can be attached to the probes disclosed herein include those provided in U.S. Pat. No. 5,866,366 to Nazarenko et al., such as 4-acetamido-4'-isothiocyanatostilbene-2,2'disulfonic acid; acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), -6-carboxy-fluorescein (HEX), and TET (Tetramethyl fluorescein); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (CIBACRON™. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red); riboflavin; rosolic acid and terbium chelate derivatives; Cy5.5; Cy56-carboxyfluorescein; boron dipyrromethene difluoride (BODIPY); acridine; stilbene; Texas Red®; Cy3®; Cy5®, VIC® (Applied Biosystems); LC Red 640; LC Red 705; and Yakima yellow, amongst others.

Other suitable fluorophores include those known, for example those available from Molecular Probes (Eugene, Oreg.). In particular examples, a fluorophore is used as a donor fluorophore or as an acceptor fluorophore.

B. Primers for Amplification of Influenza Virus Nucleic Acids

Primers capable of hybridizing to and directing the amplification of influenza virus nucleic acid molecules are disclosed. The primers disclosed herein are between 15 to 40 nucleotides in length, such as 15, 16, 17, 18, 19, 20, 21, 22, 23, 24, 25, 26, 27, 28, 29, 30, 31, 32, 33, 34, 35, 36, 37, 38, 39, or 40 nucleotides in length. In some embodiments, a primer is capable of hybridizing under high or very high stringency conditions to an influenza virus nucleic acid molecule and directing the amplification of the influenza nucleic acid molecule or a portion thereof.

A primer capable of hybridizing to and directing the amplification of an influenza nucleic acid molecule includes a nucleic acid sequence that is at least 90% identical such as at least 91%, at least 92%, at least 93%, at least 94%, at least 95%, at least 96%, at least 97%, at least 98%, at least 99%, or even 100% identical to the nucleic acid sequence of SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 14, SEQ ID NO: 15, SEQ ID NO: 16, SEQ ID NO: 17, SEQ ID NO: 20, SEQ ID NO: 21, SEQ ID NO: 23, SEQ ID NO: 24, SEQ ID NO: 26, SEQ ID NO: 27, SEQ ID NO: 29, SEQ ID NO: 30, SEQ ID NO: 32, or SEQ ID NO: 33. In some embodiments, a primer capable of hybridizing to an influenza nucleic acid molecule consists of or consists essentially of a nucleic acid sequence of SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 14, SEQ ID NO: 15, SEQ ID NO: 16, SEQ ID NO: 17, SEQ ID NO: 20, SEQ ID NO: 21, SEQ ID NO: 23, SEQ ID NO: 24, SEQ ID NO: 26, SEQ ID NO: 27, SEQ ID NO: 29, SEQ ID NO: 30, SEQ ID NO: 32, or SEQ ID NO: 33.

In some embodiments, the primer is influenza subtype-specific. An influenza subtype-specific primer is capable of hybridizing under stringent conditions (such as high stringency or very high stringency conditions) to an influenza virus nucleic acid from a specific influenza subtype, such as influenza HA sequence that is subtype-specific for H1 pandemic 2009. Subtype-specific primers can be used to amplify sequences specific to the various influenza subtypes. In some examples, a primer that is subtype-specific for (for example, hybridizes to) influenza subtype H1, such as influenza subtype H1 pandemic 2009, is not subtype-specific for (for example, does not substantially hybridize to) other influenza HA subtypes, such as seasonal H1 subtype, H3 (seasonal and/or variant), subtype H5, subtype H7 (Eurasian or North American) or subtype H9. One of ordinary skill in the art will understand that subtype-specific primers, such as those disclosed herein are also not subtype-specific for (for example, do not hybridize to) other influenza virus subtypes.

In a specific example, a primer specific for an influenza subtype H1 pandemic 2009 nucleic acid includes or consists of a nucleic acid sequence at least 90% identical (such as a nucleic acid sequence at least 91%, at least 92%, at least 93%, at least 94%, at least 95%, at least 96%, at least 97%, at least 98%, at least 99%, or even 100% identical) to SEQ ID NO: 1 or SEQ ID NO: 2.

In certain embodiments the primers are included in a set of primers, such as a pair of primers, capable of hybridizing to and amplifying an influenza nucleic acid. Such a set of primers includes at least one forward primer and at least one reverse primer, where the primers are specific for the amplification of an influenza subtype nucleic acid molecule. In some examples, the set of primers includes at least one pair of primers that is specific for the amplification of an influenza subtype H1 pandemic 2009 nucleic acid sequence. In some examples, the set of primers further includes at least one or more pairs of primers that are specific for the amplification of other types or subtypes, such as influenza type A, influenza type A pandemic 2009, influenza subtype H3, subtype H5, subtype Eurasian H7, subtype North American H7, subtype H9, influenza B, or two or more thereof.

In certain examples, the pair of primers is specific for the amplification of an influenza subtype H1 pandemic 2009 nucleic acid and includes a forward primer at least 90% identical (such as a nucleic acid molecule at least 91%, at least 92%, at least 93%, at least 94%, at least 95%, at least 96%, at least 97%, at least 98%, at least 99% or even 100% identical) to SEQ ID NO: 1 and a reverse primer at least 90% identical (such as a nucleic acid sequence at least 91%, at least 92%, at least 93%, at least 94%, at least 95%, at least 96%, at least 97%, at least 98%, at least 99% or even 100% identical) to SEQ ID NO: 2.

In some examples, the set of primers further includes one or more additional influenza type or subtype-specific primers (such as one or more primer pairs), such as primers that are specific the amplification of one or more of influenza type A, influenza type B, 2009 pandemic influenza type A, influenza type B, influenza virus H3 (seasonal or variant), influenza subtype H5, influenza subtype H7 (Eurasian or North American), and/or influenza subtype H9 (e.g., see sequences provided in Table 1). In additional embodiments, the set of primers includes one or more control primers, such as one or more primers specific for a control human nucleic acid molecule (for example, RNase P, such as RNase P forward and reverse primers SEQ ID NOS: 35 and 36).

Although exemplary probes and primers are provided in SEQ ID NOs: 1-34, one skilled in the art will appreciate that the primer or probe sequences can be varied slightly by moving the probe or primer a few nucleotides upstream or downstream from the nucleotide positions that they hybridize to on the influenza nucleic acid, provided that the probe or primer is still specific for the influenza sequence, such as specific for the subtype of the influenza sequence. For example, one of ordinary skill in the art will appreciate that by analyzing sequence alignments of influenza type or subtype genes (for example HA gene sequences), that variations of the probes or primers disclosed herein can be made for example, by "sliding" the probes and/or primers a few nucleotides 5' or 3' from their positions, and that such variation will still be specific for the influenza viral subtype.

Also provided by the present application are probes and primers that include variations to the nucleotide sequences shown in any of SEQ ID NOs: 1-34, as long as such variations permit detection of the influenza virus nucleic acid, such as an influenza subtype nucleic acid. For example, a probe or primer can have at least 90% sequence identity such as at least 91%, at least 92%, at least 93%, at least 94%, at least 95%, at least 96%, at least 97%, at least 98%, at least 99% to anucleic acid consisting of the sequence shown in any of SEQ ID NOs: 1-34. In some examples, the number of nucleotides does not change, but the nucleic acid sequence shown in any of SEQ ID NOs: 1-34 can vary at a few nucleotides, such as changes at 1, 2, 3, or 4 nucleotides.

The present application also provides probes and primers that are slightly longer or shorter than the nucleotide sequences shown in any of SEQ ID NOs: 1-34, as long as such deletions or additions permit detection or amplification of the desired influenza nucleic acid, such as an influenza subtype. For example, a probe or primer can include a few nucleotide deletions or additions at the 5'- and/or 3'-end of the probe or primer shown in any of SEQ ID NOs: 1-34, such as addition or deletion of 1, 2, 3, or 4 nucleotides from the 5'- or 3'-end, or combinations thereof (such as a deletion from one end and an addition to the other end). In such examples, the number of nucleotides may change. One of skill in the art will appreciate that sequence alignments provide sufficient guidance as to what additions and/or subtractions can be made, while still maintaining specificity for the influenza viral subtype.

Also provided are probes and primers that are degenerate at one or more positions (such as 1, 2, 3, 4, 5, or more positions), for example, a probe or primer that includes a mixture of nucleotides (such as 2, 3, or 4 nucleotides) at a specified position in the probe or primer. In other examples, the probes and/or primers include one or more synthetic bases or alternative bases (such as inosine). In other examples, the probes and/or primers disclosed herein include one or more modified nucleotides or nucleic acid analogues, such as one or more locked nucleic acids (see, e.g., U.S. Pat. No. 6,794,499) or one or more superbases (Nanogen, Inc., Bothell, Wash.). In other examples, the probes and primers disclosed herein include a minor groove binder conjugated to the 5' or 3' end of the oligonucleotide (see, e.g., U.S. Pat. No. 6,486,308).

IV. Methods of Detecting Influenza Virus Nucleic Acids

Methods for the detection of influenza nucleic acids are disclosed, for example to determine if a sample contains an influenza virus. Methods also are provided for determining the type and/or subtype of the influenza viral nucleic acid, for example to determine the type and/or subtype of influenza virus present in a sample. A particular application of the influenza virus-specific primers and probes disclosed herein is for the detection and subtyping of influenza viruses in a sample, such as a biological sample obtained from a subject that has or is suspected of having an influenza infection. Thus, in some embodiments the disclosed methods can be used to diagnose if a subject has an influenza infection and/or discriminate the viral subtype with which the subject is infected.

The methods described herein may be used for any purpose for which detection of influenza is desirable, including diagnostic and prognostic applications, such as in laboratory and clinical settings, or for detection and characterization of novel viruses infecting humans and wild or domesticated animals. Appropriate samples include any conventional environmental or biological samples, including clinical samples obtained from a human or animal subject, such as a bird (such as a chicken or turkey) or swine. Suitable samples include all biological samples useful for detection of viral infection in subjects, including, but not limited to, cells, tissues (for example, lung, liver or kidney), bone marrow aspirates, bodily fluids (for example, blood, serum, urine, cerebrospinal fluid, bronchoalveolar lavage, tracheal aspirates or swabs, sputum, nasopharyngeal aspirates or swabs, oropharyngeal aspirates or swabs, saliva), eye swabs, cervical swabs, vaginal swabs, rectal swabs, stool, and stool suspensions. Particularly suitable samples include samples obtained from bronchoalveolar lavage, tracheal aspirates, sputum, nasopharyngeal aspirates, oropharyngeal aspirates, or saliva. Standard techniques for acquisition of such samples are available. See for example, Schluger et al., *J. Exp. Med.* 176:1327-33 (1992); Bigby et al., *Am. Rev. Respir. Dis.* 133:515-18 (1986); Kovacs et al., *NEJM* 318:589-93 (1988); and Ognibene et al., *Am. Rev. Respir. Dis.* 129:929-32 (1984).

In some embodiments, detecting the presence of an influenza nucleic acid sequence in a sample includes the extraction of influenza RNA. RNA extraction relates to releasing RNA from a latent or inaccessible form in a virion, cell, or sample and allowing the RNA to become freely available. In such a state, it is suitable for effective detection and/or amplification of the influenza nucleic acid. Releasing RNA may include steps that achieve the disruption of virions containing viral RNA, as well as disruption of cells that may harbor such virions. Extraction of RNA is generally carried out under conditions that effectively exclude or inhibit any ribonuclease activity that may be present. Additionally, extraction of RNA may include steps that achieve at least a partial separation of the RNA dissolved in an aqueous medium from other cellular or viral components, wherein such components may be either particulate or dissolved.

Methods for extracting RNA from a sample can depend upon, for example, the type of sample in which the influenza RNA is found. For example, the RNA may be extracted using guanidinium isothiocyanate, such as the single-step isolation by acid guanidinium isothiocyanate-phenol-chloroform extraction of Chomczynski et al. (*Anal. Biochem.* 162:156-59, 1987). The sample can be used directly or can be processed, such as by adding solvents, preservatives, buffers, or other compounds or substances. Viral RNA can be extracted using standard methods. For instance, rapid RNA preparation can be performed using a commercially available kit (such as the MAGNA PURE® Compact Nucleic Acid Isolation Kit I (Roche Applied Science, Pleasanton, Calif.), MAGNA PURE® Compact RNA Isolation Kit (Roche Applied Science, Pleasanton, Calif.), MAGNA PURE® LC total nucleic acid kit (Roche Applied Science, Pleasanton, Calif.); QIAAMP® Viral RNA Mini Kit, QIAAMP® MinElute Virus Spin Kit or RNEASY® Mini Kit (Qiagen, Valencia, Calif.); Qiagen QIAcube QIAmp® DSP Viral RNA Mini Kit (Qiagen, Valencia, Calif.), NUCLISENS® EASYMAG® or NUCLISENS® MINIMAG® nucleic acid isolation system (bioMérieux, Durham, N.C.); ChargeSwitch® Total RNA Cell Kit (Life Technologies, Carlsbad, Calif.); or MASTERPURE™ Complete DNA and RNA Purification Kit (Epicentre Biotechnologies, Madison, Wis.)). Alternatively, an influenza virion may be disrupted by a suitable detergent in the presence of proteases and/or inhibitors of ribonuclease activity. Additional exemplary methods for extracting RNA are found, for example, in World Health Organization, *Manual for the Virological Investigation of Polio*, World Health Organization, Geneva, 2001.

Detecting an influenza virus nucleic acid in a sample includes contacting the sample with at least one of the influenza specific probes disclosed herein that is capable of hybridizing to an influenza virus nucleic acid under conditions of high stringency or very high stringency (such as a nucleic acid probe capable of hybridizing under high stringency or very high stringency conditions to an influenza nucleic acid nucleic acid, for example a probe including a nucleic acid sequence at least 90%, at least 95%, or 100% identical to the nucleotide sequence of SEQ ID NO: 3, and in some examples additionally a probe including a nucleic acid sequence at least 90%, at least 95%, or 100% identical to the nucleotide sequence of SEQ ID NO: 6 and/or SEQ ID NO: 9), and detecting hybridization between the influenza virus nucleic acid and the probe. Detection of hybridization between the probe and the influenza nucleic acid indicates the presence of the influenza nucleic acid in the sample. In some examples, detection of hybridization between the probe and the influenza virus nucleic acid in the sample diagnoses influenza virus infection in a subject, for example when the sample is a biological sample obtained from the subject, such as a subject suspected of having an influenza virus infection.

The influenza virus specific probes disclosed herein can be used to detect the presence of and/or discriminate between influenza subtypes in a sample. For example, contacting a sample with a probe specific for influenza subtype H1 pandemic 2009, such as a probe capable of hybridizing under high or very high stringency conditions to an influenza subtype H1 pandemic 2009 nucleic acid, for example a nucleic acid probe at least 90%, at least 95%, or 100% identical to the nucleotide sequence of SEQ ID NO: 3, and detecting hybridization between the probe and the influenza nucleic acid indicates that influenza A subtype H1 pandemic 2009 is present. In another example, contacting a sample with a probe capable of hybridizing under high or very high stringency conditions to an influenza type A nucleic acid, for example a nucleic acid probe at least 90%, at least 95%, or 100% identical to the nucleotide sequence of SEQ ID NO: 6, and detecting hybridization between the probe and the influenza nucleic acid indicates that influenza type A is present. In another example, contacting a sample with a probe specific for variant influenza type A pandemic 2009, for example a nucleic acid probe at least 90%, at least 95%, or 100% identical to the nucleotide sequence of SEQ ID NO: 9, and detecting hybridization between the probe and the influenza nucleic acid indicates the presence of influenza type A pandemic 2009.

In some embodiments, the methods further include contacting the sample with additional influenza type-specific and/or influenza subtype-specific probes to further detect or discriminate the type and/or subtype of influenza virus nucleic acid in the sample. In some embodiments, the methods further include contacting the sample with one or more influenza type-specific probes, such as one or more probes specific for influenza type B and/or one or more additional influenza subtype-specific probes, such as one or more probes specific for influenza subtype H1, influenza subtype H3 (seasonal or variant), influenza subtype H5, influenza subtype H7 (Eurasian or North American), and/or influenza subtype H9. Exemplary additional probes suitable for the methods disclosed herein are disclosed in International Pat. Publ. No. WO 2007/095155 as shown in Table 1.

In some examples, an influenza subtype H1 pandemic 2009 specific probe includes a nucleic acid capable of hybridizing under high stringency or very high stringency to an influenza subtype H1 pandemic 2009 HA gene sequence. In some examples, the influenza subtype H1 pandemic 2009 specific probe disclosed herein includes a nucleic acid at least 90% identical (such as a nucleic acid at least 91%, 92%, 93%, 94%, 95%, 96%, 97%, 98%, 99%, or even 100% identical) to the sequence ATACATCCRATCACAATTGGRAAATGTCCAAA (SEQ ID NO: 3). In some examples, an influenza A type-specific probe includes a nucleic acid capable of hybridizing under high stringency or very high stringency to an influenza type A M gene sequence. In some examples, the influenza A type-specific probe includes a nucleic acid at least 90% identical (such as a nucleic acid at least 91%, 92%, 93%, 94%, 95%, 96%, 97%, 98%, 99%, or even 100% identical) to the sequence TGCAGTCCTCGCTCACTGGGCACG (SEQ ID NO: 6). In other examples, an influenza A type-specific probe is a 2009 pandemic influenza A type-specific probe that includes a nucleic acid capable of hybridizing under high stringency or very high stringency to an influenza type A NP gene sequence. In some examples, the influenza A pandemic 2009 type-specific probe includes a nucleic acid at least 90% identical (such as a nucleic acid at least 91%, 92%, 93%, 94%, 95%, 96%, 97%, 98%, 99%, or even 100% identical) to the sequence TGAATGGGTCTATCCCGACCAGTGAGTAC (SEQ ID NO: 9).

In some examples, the methods also include contacting the sample with a positive control probe, such as a probe capable of hybridizing to a human nucleic acid, for example when the subject is a human. In some examples, the positive control probe is a probe capable of hybridizing to a human RNase P nucleic acid, such as SEQ ID NO: 37.

In some embodiments, the probe is detectably labeled (e.g., has a label covalently or non-covalently attached thereto), either with an isotopic or non-isotopic label; in alternative embodiments, the influenza nucleic acid is labeled. Non-isotopic labels can, for instance, comprise a fluorescent or luminescent molecule, or an enzyme, co-factor, enzyme substrate, or hapten. The probe is incubated with a single-stranded or double-stranded preparation of RNA, DNA, or a mixture of both, and hybridization determined. In some examples the hybridization results in a detectable change in signal such as in increase or decrease in signal, for example from the labeled probe. Thus, detecting hybridization comprises detecting a change in signal from the labeled probe during or after hybridization relative to signal from the label before hybridization.

In some embodiments, influenza virus nucleic acids present in a sample are amplified prior to or substantially simultaneously with using a hybridization probe for detection. For instance, a portion of the influenza virus nucleic acid can be amplified to increase the number of nucleic acids that can be detected, thereby increasing the signal obtained, and the amplified influenza virus nucleic acid detected. Influenza specific nucleic acid primers can be used to amplify a region that is at least about 50, at least about 60, at least about 70, at least about 80 at least about 90, at least about 100, at least about 200, at least about 300, or more base pairs in length to produce amplified influenza specific nucleic acids. Any nucleic acid amplification method can be used to detect the presence of influenza in a sample. In one specific, non-limiting example, polymerase chain reaction (PCR) is used to amplify the influenza nucleic acid sequences. In other specific, non-limiting examples, real-time PCR, reverse transcriptase-polymerase chain reaction (RT-PCR), real-time reverse transcriptase-polymerase chain reaction (rRT-PCR), ligase chain reaction, or transcription-mediated amplification is used to amplify the influenza nucleic acid. In a specific example, the influenza virus nucleic acid is amplified by rRT-PCR.

Typically, at least two primers are utilized in the amplification reaction, however, one primer can be utilized, for example to reverse transcribe a single stranded nucleic acid such as a single-stranded influenza RNA. Amplification of the influenza nucleic acid involves contacting the influenza nucleic acid with one or more primers that are capable of hybridizing to and directing the amplification of an influenza nucleic acid (such as a nucleic acid capable of hybridizing under high stringency or very high stringency conditions to an influenza nucleic acid, for example a primer that is least 90% identical to the nucleotide sequence of any one of SEQ ID NO: 1, SEQ ID NO: 2, SEQ ID NO: 4, SEQ ID NO: 5, SEQ ID NO: 7, or SEQ ID NO: 8). In some embodiments, the sample is contacted with at least one primer that is specific for an influenza subtype, such as those disclosed herein.

In some embodiments, the sample is contacted with at least one pair of primers that include a forward and reverse primer that both hybridize to an influenza nucleic acid specific for an influenza type A, an influenza type A pandemic 2009, or an influenza subtype H1 pandemic 2009. Examples of suitable primer pairs for the amplification of influenza subtype-specific nucleic acids are described above in Section IIIB.

In additional embodiments, the methods further include amplifying one or more influenza type-specific and/or influenza subtype-specific nucleic acids to further detect or discriminate the type and/or subtype of influenza virus nucleic acid in the sample. In some embodiments, the methods further include contacting the sample with one or more additional influenza type-specific primers, such as one or more primers specific for influenza type A, 2009 pandemic influenza type A and/or influenza type B and/or one or more influenza subtype-specific primers specific, such as one or more primers specific for 2009 pandemic influenza subtype H1, influenza subtype H3, influenza subtype H5, influenza subtype H7, and/or influenza subtype H9. Exemplary additional primers suitable for the methods disclosed herein are disclosed in International Pat. Publ. No. WO 2007/095155, and in Table 1.

In some embodiments, the methods further include contacting the sample with one or more primers capable of hybridizing to and directing the amplification of an influenza H1 pandemic 2009 nucleic acid molecule (such as an influenza subtype H1 pandemic 2009 HA gene nucleic acid) and includes a nucleic acid sequence that is at least 90% identical, such as at least 91%, 92%, 93%, 94%, 95%, 96%, 97%, 98%, 99%, or even 100% identical, to the nucleic acid sequence GTGCTATAAACACCAGCCTCCCATT (SEQ ID NO: 1) or AGAYGGGACATTCCTCAATCCTG (SEQ ID NO: 2). In several embodiments, a pair of primers capable of hybridizing to and directing the amplification of a 2009 pandemic influenza H1 nucleic acid molecule includes the primers of SEQ ID NO: 1 and SEQ ID NO: 2.

In some embodiments, the methods further include contacting the sample with one or more primers capable of hybridizing to and directing the amplification of an influenza type A nucleic acid molecule (such as an influenza type A M gene nucleic acid) and includes a nucleic acid sequence that is at least 90% identical, such as at least 91%, 92%, 93%, 94%, 95%, 96%, 97%, 98%, 99%, or even 100% identical, to the nucleic acid sequence GACCRATCCTGTCACCTCTGAC (SEQ ID NO: 4) or AGGGCATTYTGGACAAAKCGTCTA (SEQ ID NO: 5). In several embodiments, a pair of primers capable of hybridizing to and directing the amplification of an influenza type A nucleic acid molecule includes the primers of SEQ ID NO: 4 and SEQ ID NO: 5.

In additional embodiments, the methods further include contacting the sample with one or more primers capable of hybridizing to and directing the amplification of an influenza type A pandemic 2009 nucleic acid molecule (such as influenza pandemic 2009 type A NP gene nucleic acid) and includes a nucleic acid sequence that is at least 90% identical, such as at least 91%, 92%, 93%, 94%, 95%, 96%, 97%, 98%, 99%, or even 100% identical, to the nucleic acid sequence TTGCAGTAGCAAGTGGGCATGA (SEQ ID NO: 7) or TCTTGTGAGCTGGGTTTTCATTTG (SEQ ID NO: 8). In several embodiments, a pair of primers capable of hybridizing to and directing the amplification of an influenza type A pandemic 2009 nucleic acid molecule includes the primers of SEQ ID NO: 7 and SEQ ID NO: 8.

In further embodiments, the methods further include contacting the sample with one or more primers capable of hybridizing to and directing the amplification of an influenza subtype H1, seasonal and/or variant H3, H5, Eurasian and/or North American H7 and/or H9 as disclosed in PCT/US2014/061802 and in Table 1.

In further embodiments, the methods also include contacting the sample with one or more positive control primers capable of hybridizing to and directing the amplification of a human RNase P nucleic acid molecule (e.g., SEQ ID NOs: 35 and 36).

Any type of thermal cycler apparatus can be used for the amplification of the influenza nucleic acids and/or the determination of hybridization. Examples of suitable apparatuses include a PTC-100® Peltier Thermal Cycler (MJ Research, Inc.; San Francisco, Calif.), a ROBOCYCLER® 40 Temperature Cycler (Stratagene; La Jolla, Calif.), or a GENEAMP® PCR System 9700 (Applied Biosystems; Foster City, Calif.). For real-time PCR, any type of real-time thermocycler apparatus can be used. For example, a BioRad iCycler iQ™, LIGHTCYCLER™ (Roche; Mannheim, Germany), a 7700 Sequence Detector (Perkin Elmer/Applied Biosystems; Foster City, Calif.), ABI™ systems such as the 7000, 7500, 7700, or 7900 systems (Applied Biosystems; Foster City, Calif.), ABI™ system 7500 Fast Dx Real-Time PCR Instrument with SDS software version 1.4 ((Applied Biosystems; Foster City, Calif.), an MX4000™, MX3000™ or MX3005™ (Stratagene; La Jolla, Calif.), and Cepheid SMARTCYCLER™ can be used to amplify nucleic acid sequences in real-time.

The amplified influenza nucleic acid, for example an influenza type or subtype-specific nucleic acid, can be detected in real-time, for example by real-time PCR such as real-time RT-PCR, in order to determine the presence, the identity, and/or the amount of an influenza type or subtype-specific nucleic acid in a sample. In this manner, an amplified nucleic acid sequence, such as an amplified influenza nucleic acid sequence, can be detected using a probe specific for the product amplified from the influenza sequence of interest, such as an influenza sequence that is specific for 2009 pandemic influenza subtype H1, influenza type A, 2009 pandemic influenza type A, type B, subtype H1, H3 (seasonal or variant), H5, North American H7, Eurasian H7, and/or H9. Detecting the amplified product includes the use of labeled probes that are sufficiently complementary and hybridize to the amplified nucleic acid sequence. Thus, the presence, amount, and/or identity of the amplified product can be detected by hybridizing a labeled probe, such as a fluorescently labeled probe, complementary to the amplified product. In one embodiment, the detection of a target nucleic acid of interest includes the combined use of PCR amplification and a labeled probe such that the product is measured using real-time RT-PCR. In another embodiment, the detection of an amplified target nucleic acid of interest includes the transfer of the amplified target nucleic acid to a solid support, such as a blot, for example a Northern blot or Southern blot, and probing the blot with a probe, for example a labeled probe, that is complementary to the amplified target nucleic acid. In yet another embodiment, the detection of an amplified target nucleic acid of interest includes the hybridization of a labeled amplified target nucleic acid to probes disclosed herein that are an arrayed in a predetermined array with an addressable location and that are complementary to the amplified target nucleic acid.

In one embodiment, fluorescently-labeled probes rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a fluorophore and a non-fluorescent quencher on the same probe (for example, using a molecular beacon or a TAQMAN® probe) can identify a probe that specifically hybridizes to the nucleic acid of interest and in this way, using influenza type and/or subtype-specific probes, can detect the presence, identity, and/or amount of an influenza type and/or subtype in a sample. In one embodiment, fluorescently-labeled DNA probes used to identify amplification products have spectrally distinct emission wavelengths, thus allowing them to be distinguished within the same reaction tube (for example, using multiplex PCR, multiplex RT-PCR or multiplex rRT-PCR).

In another embodiment, a melting curve analysis of the amplified target nucleic acid can be performed subsequent to the amplification process. The $T_m$ of a nucleic acid sequence depends on the length of the sequence and its G/C content. Thus, the identification of the $T_m$ for a nucleic acid sequence can be used to identify the amplified nucleic acid.

In some examples, the disclosed methods can predict with a sensitivity of at least 90% and a specificity of at least 90% for presence of an influenza virus nucleic acid. In some examples, the disclosed methods can predict with a sensitivity of at least 90% and a specificity of at least 90% for presence of an influenza subtype H1 pandemic 2009 virus nucleic acid, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%. In other examples, the disclosed methods can predict with a sensitivity of at least 90% and a specificity of at least 90% for presence of a subtype H1 pandemic 2009 virus nucleic acid and one or more additional influenza nucleic acids such as an influenza type A, influenza type A pandemic 2009, subtype H1, H3 (seasonal or variant), H5, H7 (Eurasian or North American), or H9 nucleic acid, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%.

In other examples, disclosed methods can detect presence of an influenza subtype H1 pandemic 2009 nucleic acid in a sample with a limit of detection (LOD) of about $10^{0.4}$-$10^8$ $EID_{50}$/ml, $10^1$-$10^8$ $EID_{50}$/ml, about $10^4$-$10^7$ $EID_{50}$/ml, about $10^1$-$10^4$ $EID_{50}$/ml, about $10^2$-$10^5$ $EID_{50}$/ml, or about $10^3$-$10^6$ $EID_{50}$/ml (such as about $10^{0.4}$, $10^1$, $10^2$, $10^3$, $10^4$, $10^5$, $10^6$, $10^7$, or $10^8$ $EID_{50}$/ml). In other examples the disclosed methods can detect one or more additional influenza nucleic acids such as an influenza type A, a 2009 pandemic influenza type A, an influenza subtype H3 (seasonal or variant), H5, H7 (Eurasian or North American), or H9 nucleic acid in a sample with a limit of detection (LOD) of about $10^{0.4}$-$10^8$ $EID_{50}$/ml, $10^1$-$10^8$ $EID_{50}$/ml, about $10^4$-$10^7$ $EID_{50}$/ml, about $10^1$-$10^4$ $EID_{50}$/ml, about $10^2$-$10^5$ $EID_{50}$/ml, or about $10^3$-$10^6$ $EID_{50}$/ml (such as about $10^{0.4}$, $10^1$, $10^2$, $10^3$, $10^4$, $10^5$, $10^6$, $10^7$, or $10^8$ $EID_{50}$/ml).

In additional embodiments, the disclosed methods can further include or can be used in conjunction with methods for detecting the presence of one or more additional respiratory viral or bacterial nucleic acids in the sample. In some examples, the presence of one or more additional viral nucleic acids, including but not limited to rhinovirus, coronavirus, respiratory syncytial virus, adenovirus, or parainfluenza virus, are detected. In other examples, the presence of bacterial nucleic acids, for example, respiratory bacteria, including but not limited to *Legionella, Haemophilus influenzae, Streptococcus pneumoniae, Mycoplasma pneumoniae*, or *Chlamydophila pneumoniae*, are detected.

V. Arrays

Arrays containing a plurality of heterogeneous probes for the detection, typing, and/or subtyping of influenza viruses are disclosed. Such arrays may be used to rapidly detect and/or identify the type and/or subtype of an influenza virus in a sample. For example the arrays can be used to determine the presence of subtype H1 pandemic 2009 in a sample. Such arrays may also be used to determine the presence of 2009 pandemic influenza subtype H1 in a sample, further including one or more of the viruses influenza A, and/or 2009 pandemic influenza A, and/or any one or more of influenza B, influenza subtypes H1, H3 (seasonal or variant), H5, H7 (North American or Eurasian), and H9.

Arrays are arrangements of addressable locations on a substrate, with each address containing a nucleic acid, such as a probe. In some embodiments, each address corresponds to a single type or class of nucleic acid, such as a single probe, though a particular nucleic acid may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

In some embodiments, an influenza profiling array includes one or more influenza subtype-specific probes (such as 1, 2, 3, 4, 5, 6, 7, 8, 9, 10, 11, 12, 13, 14, 15, 20, 25, 50, 100, or more probes), including at least one probe capable of detecting 2009 pandemic influenza subtype H1. In some embodiments, the one or more specific probes detect, in addition to detecting 2009 pandemic influenza subtype H1, additional influenza type or subtype nucleic acids including one or more of influenza type A, 2009 pandemic influenza type A, influenza B, subtypes H1, seasonal H3, variant H3, H5, Eurasian H7, North American H7, and/or H9. In some examples, the array includes 1, 2, 3, or more probes at least 90%, at least 95%, at least 96%, at least 97%, at least 98%, at least 99%, or 100% identical to the nucleic acid sequence of SEQ ID NO: 3 for the detection of 2009 pandemic subtype H1 and, may further include SEQ ID NO: 6 and/or SEQ ID NO: 9 for the additional detection of influenza type A and/or 2009 pandemic influenza type A. In some examples, the array includes all of the probes of SEQ ID NO: 3, SEQ ID NO: 6, and SEQ ID NO: 9. In some examples, the one more probe sequences are in separate wells of a multi-well plate. In other examples, the one or more probes are covalently attached to a substrate, directly or indirectly.

In some embodiments, the array includes one or more 2009 pandemic subtype H1 probe. In some examples, the array further includes, in addition to the one or more 2009 pandemic subtype H1 probe, one or more influenza virus type-specific or subtype-specific probes other than a subtype H1 pandemic 2009 probe, such as one or more probes for the additional detection of influenza A, 2009 pandemic influenza A, influenza type B, subtype H1, seasonal or variant influenza subtype H3, subtype H5, subtype H7 (Eurasian or North American), influenza subtype H9, and/or other subtypes known to one of ordinary skill in the art. Thus, in some examples, the array includes the probe of SEQ ID NO: 3, and one or more of the following probe sequences: SEQ ID NO: 6, SEQ ID NO: 9 SEQ ID NO: 12, SEQ ID NO: 13, SEQ ID NO: 18, SEQ ID NO: 19, SEQ ID NO: 22, SEQ ID NO: 25, SEQ ID NO: 28, SEQ ID NO: 31, and SEQ ID NO: 34 (such as 1, 2, 3, 4, 5, 6, 7, 8, 9, 10 or 11 of these).

In further embodiments, the array also includes one or more control probes, such as one or more positive or negative control probes. In one example, the array includes at least one positive control probe, such as a probe capable of hybridizing to a human nucleic acid, such as RNase P probe (SEQ ID NO: 37).

In some embodiments, an influenza profiling array is a collection of separate probes at the array addresses. The influenza profiling array is then contacted with a sample suspected of containing influenza nucleic acids under conditions allowing hybridization between the probe and nucleic acids in the sample to occur. Any sample potentially containing, or even suspected of containing, influenza nucleic acids may be used, including nucleic acid extracts, such as amplified or non-amplified DNA or RNA preparations. A hybridization signal from an individual address on the array (such as a well) indicates that the probe hybridizes to a nucleotide within the sample. This system permits the simultaneous analysis of a sample by plural probes and yields information identifying the influenza nucleic acids contained within the sample. In alternative embodiments, the array contains influenza nucleic acids and the array is contacted with a sample containing a probe. In any such embodiment, either the probe or the influenza nucleic acids may be labeled to facilitate detection of hybridization.

The nucleic acids may be added to an array substrate in dry or liquid form. Other compounds or substances may be added to the array as well, such as buffers, stabilizers, reagents for detecting hybridization signal, emulsifying agents, or preservatives.

In certain examples, the array includes one or more molecules or samples (such as one or more probes) occurring on the array a plurality of times (twice or more) to provide an added feature to the array, such as redundant activity or to provide internal controls.

Within an array, each arrayed nucleic acid is addressable, such that its location may be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

An address within the array may be of any suitable shape and size. In some embodiments, the nucleic acids are suspended in a liquid medium and contained within square or rectangular wells on the array substrate. However, the nucleic acids may be contained in regions that are essentially triangular, oval, circular, or irregular. The overall shape of the array itself also may vary, though in some embodiments it is substantially flat and rectangular or square in shape.

Influenza profiling arrays may vary in structure, composition, and intended functionality, and may be based on either a macroarray or a microarray format, or a combination thereof. Such arrays can include, for example, at least 1, at least 2, at least 3, at least 4, at least 5, at least 10, at least 15, at least 20, at least 25, at least 50, at least 100, or more addresses, usually with a single type of nucleic acid at each address. In one example, the array is a 96-well plate. In the case of macroarrays, sophisticated equipment is usually not required to detect a hybridization signal on the array, though quantification may be assisted by standard scanning and/or quantification techniques and equipment. Thus, macroarray analysis as described herein can be carried out in most hospitals, agricultural and medical research laboratories, universities, or other institutions without the need for investment in specialized and expensive reading equipment.

Examples of substrates for the arrays disclosed herein include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (for example glass or a supported membrane) or flexible (such as a polymer membrane). In some examples, the array substrate is a multi-well plate, such as a 96-well plate or a 384-well plate.

Addresses on the array should be discrete, in that hybridization signals from individual addresses can be distinguished from signals of neighboring addresses, either by the naked eye (macroarrays) or by scanning or reading by a piece of equipment or with the assistance of a microscope (microarrays).

Addresses in an array may be of a relatively large size, such as large enough to permit detection of a hybridization signal without the assistance of a microscope or other equipment. Thus, addresses may be as small as about 0.1 mm across, with a separation of about the same distance. Alternatively, addresses may be about 0.5, 1, 2, 3, 5, 7, or 10 mm across, with a separation of a similar or different distance. Larger addresses (larger than 10 mm across) are employed in certain embodiments. The overall size of the array is generally correlated with size of the addresses (for example, larger addresses will usually be found on larger arrays, while smaller addresses may be found on smaller arrays). Such a correlation is not necessary, however.

The arrays herein may be described by their densities (the number of addresses in a certain specified surface area). For macroarrays, array density may be about one address per square decimeter (or one address in a 10 cm by 10 cm region of the array substrate) to about 50 addresses per square centimeter (50 targets within a 1 cm by 1 cm region of the substrate). For microarrays, array density will usually be one or more addresses per square centimeter, for instance, about 50, about 100, about 200, about 300, about 400, about 500, about 1000, about 1500, about 2,500, or more addresses per square centimeter.

The use of the term "array" includes the arrays found in DNA microchip technology. As one, non-limiting example, the probes could be contained on a DNA microchip similar to the GENECHIP® products and related products commercially available from Affymetrix, Inc. (Santa Clara, Calif.). Briefly, a DNA microchip is a miniaturized, high-density array of probes on a glass wafer substrate. Particular probes are selected, and photolithographic masks are designed for use in a process based on solid-phase chemical synthesis and photolithographic fabrication techniques similar to those used in the semiconductor industry. The masks are used to isolate chip exposure sites, and probes are chemically synthesized at these sites, with each probe in an identified location within the array. After fabrication, the array is ready for hybridization. The probe or the nucleic acid within the sample may be labeled, such as with a fluorescent label and, after hybridization, the hybridization signals may be detected and analyzed.

VI. Kits

The nucleic acid primers and probes disclosed herein can be supplied in the form of a kit for use in the detection, typing, and/or subtyping of influenza, including kits for any of the arrays described above. In such a kit, an appropriate amount of one or more of the nucleic acid probes and/or primers is provided in one or more containers or held on a substrate. A nucleic acid probe and/or primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, multi-well plates, ampoules, or bottles. The kits can include either labeled or unlabeled nucleic acid probes for use in detection, typing, and/or subtyping of influenza nucleic acids (such as those disclosed herein). The kits can additionally include one or more control probes and/or primers, for example for the detection of human RNase P.

In some embodiments, one or more primers (as described above), such as pairs of primers, may be provided in pre-measured single use amounts in individual, typically disposable, wells, tubes, or equivalent containers. With such an arrangement, the sample to be tested for the presence of influenza nucleic acids can be added to the individual tubes or wells and amplification carried out directly.

The amount of nucleic acid primer supplied in the kit can be any appropriate amount, and may depend on the target market to which the product is directed. For instance, if the kit is adapted for research or clinical use, the amount of each nucleic acid primer provided would likely be an amount sufficient to prime several PCR amplification reactions. General guidelines for determining appropriate amounts may be found in Innis et al., Sambrook et al., and Ausubel et al. A kit may include more than two primers in order to facilitate the PCR amplification of a larger number of influenza nucleotide sequences.

In some embodiments, kits also may include the reagents necessary to carry out hybridization and/or PCR amplification reactions, including DNA sample preparation reagents, polymerase (such as Taq polymerase), appropriate buffers (such as polymerase buffer), salts (for example, magnesium chloride), and deoxyribonucleotides (dNTPs).

Particular embodiments include a kit for detecting and typing and/or subtyping an influenza nucleic acid based on the arrays described above. Such a kit includes at least one probe specific for an influenza nucleic acid (as described above) and instructions. A kit may contain more than one different probe, such as 2, 3, 4, 5, 6, 7, 8, 9, 10, 11, 12, 13, 14, 15, 20, 25, 50, 100, or more probes. The instructions may include directions for obtaining a sample, processing the sample, preparing the probes, and/or contacting each probe with an aliquot of the sample. In certain embodiments, the kit includes an apparatus for separating the different probes, such as individual containers (for example, microtubules) or an array substrate (such as, a 96-well or 384-well microtiter plate). In particular embodiments, the kit includes prepackaged probes, such as probes suspended in suitable medium in individual containers (for example, individually sealed tubes) or the wells of an array substrate (for example, a 96-well microtiter plate sealed with a protective plastic film). In some embodiments, the probes are included on an array, such as the arrays described above. In other particular embodiments, the kit includes equipment, reagents, and instructions for extracting and/or purifying nucleotides from a sample.

In particular examples, the kits disclosed herein include at least one probe for the detection of aa 2009 pandemic influenza subtype H1 virus in a sample, such as one or more (such as 1, 2, 3, 4, 5, 6, 7, 8, 9, 10, or more) probes having a nucleic acid sequence at least 90% identical to the sequences of SEQ ID NO: 3. In some examples, the kits further include at least one primer for the amplification of an influenza virus nucleic acid, for example one or more primers (such as 1, 2, 3, 4, 5, 6, 7, 8, 9, 10, or more) primers having a nucleic acid sequence at least 90% identical to the sequences of SEQ ID NO: 1 or SEQ ID NO: 2. The kit includes one or more pairs of primers including SEQ ID NO: 1 and SEQ ID NO: 2. The kit may further include SEQ ID NO: 4 and SEQ ID NO: 5 or SEQ ID NO: 7 and SEQ ID NO: 8 or other primer pairs capable of amplifying influenza subtype or type nucleic acid other than 2009 pandemic influenza A subtype H1 nucleic acid, such as nucleic acid from influenza type B, influenza subtype H1, seasonal or variant influenza subtype H3, subtype H5, subtype H7 (Eurasian or North American), subtype H9 and other subtypes known to one of ordinary skill in the art.

In one specific embodiment, the kit includes at least one probe having a nucleic acid sequence at least 90%, at least 95%, at least 96%, at least 97%, at least 98%, at least 99%, or 100% identical to the sequence of SEQ ID NO: 3 and a pair of primers having a nucleic acid sequence at least 90%, at least 95%, at least 96%, at least 97%, at least 98%, at least 99%, or 100% identical to the sequence of SEQ ID NO: 1 and SEQ ID NO: 2. In other embodiments, the kit further includes at least one probe having a nucleic acid sequence at least 90%, at least 95%, at least 96%, at least 97%, at least 98%, at least 99%, or 100% identical to the sequence of SEQ ID NO: 6 and at least one pair of primers having a nucleic acid sequence at least 90%, at least 95%, at least 96%, at least 97%, at least 98%, at least 99%, or 100% identical to the sequence of SEQ ID NO: 4 and SEQ ID NO: 5, and/or at least one probe having a nucleic acid sequence at least 90%, at least 95%, at least 96%, at least 97%, at least 98%, at least 99%, or 100% identical to the sequence of SEQ ID NO: 9 and at least one pair of primers having a nucleic acid sequence at least 90%, at least 95%, at least 96%, at least 97%, at least 98%, at least 99%, or 100% identical to the sequence of SEQ ID NO: 7 and SEQ ID NO: 8.

In some examples, the kit includes the probe of SEQ ID NO: 3, and one or more of the following probe sequences: SEQ ID NO: 6, SEQ ID NO: 9 SEQ ID NO: 12, SEQ ID NO: 13, SEQ ID NO: 18, SEQ ID NO: 19, SEQ ID NO: 22, SEQ ID NO: 25, SEQ ID NO: 28, SEQ ID NO: 31, and SEQ ID NO: 34 (such as 1, 2, 3, 4, 5, 6, 7, 8, 9, 10 or 11 of these).

In some examples, the kit includes the primers of SEQ ID NOs: 1 and 2, and one or more of the following primer sequences: SEQ ID NO: 4, SEQ ID NO: 5, SEQ ID NO: 7, SEQ ID NO: 8, SEQ ID NO: 10, SEQ ID NO: 11, SEQ ID NO: 14, SEQ ID NO: 15, SEQ ID NO: 16, SEQ ID NO: 17, SEQ ID NO: 20, SEQ ID NO: 21, SEQ ID NO: 23, SEQ ID NO: 24, SEQ ID NO: 26, SEQ ID NO: 27, SEQ ID NO: 29, SEQ ID NO: 30, SEQ ID NO: 32, or SEQ ID NO: 33 (such as 1, 2, 3, 4, 5, 6, 7, 8, 9, 10, 11, 12, 13, 14, 15, 16, 17, 18, 19, or 20 of these).

One skilled in the art will appreciate that the kit can be designed to detect one or more particular influenza subtypes, using the probe and primer sequences provided herein. For example, as a non-limiting example, if the kit includes the ability to detect European H7, the kit can include the probe of SEQ ID NO: 25 and the primers shown in SEQ ID NOs: 23 and/or 24, in addition to the probe of SEQ ID NO: 3 and the primers shown in SEQ ID NOs: 1 and/or 2.

The disclosed kits may further include one or more additional probes and/or primers, for example for the detection and/or discrimination or for the further typing and/or subtyping of influenza virus nucleic acids in a sample. The kits may additionally include one or more control probes and/or primers, for example for the detection of a human nucleic acid, such as a human RNase P nucleic acid (such as 1, 2, or 3 of SEQ ID NOs: 35, 36, and 37).

In some examples, the kits may include materials for obtaining, collecting, or storing a sample, such as lancets, needles, syringes, microscope slides, blood collection tubes, and the like.

VII. Additional Probes and Primers

In some examples, the methods, devices, and kits provided herein include one or more additional probes, one or more additional forward primers, one or more additional reverse primers, or combinations thereof. For example, additional probes and primers can be used in the methods, or be part of the kits or devices, for example to permit detection of additional influenza viruses, such as influenza type B, influenza subtype H1, seasonal or variant influenza subtype H3, subtype H5, subtype H7 (Eurasian or North American), and subtype H9.

Examples of such probes and primers are provided in Table 1. Thus, in some examples, the disclosed methods further include determining if an influenza virus is the H3 subtype, by using the forward primer shown in SEQ ID NO: 10, the reverse primer shown in SEQ ID NO: 11, the probe shown in SEQ ID NO: 12 and/or 13, or combinations thereof. In some examples, the disclosed methods further include determining if an influenza virus is the H5 subtype, by using the forward primer shown in SEQ ID NO: 14 or 15, the reverse primer shown in SEQ ID NO: 16 or 17, the probe shown in SEQ ID NO: 18 and/or 19, or combinations thereof (H5 assay A). In some examples, the disclosed methods further include determining if an influenza virus is the H5 subtype, by using the forward primer shown in SEQ ID NO: 20, the reverse primer shown in SEQ ID NO: 21, the probe shown in SEQ ID NO: 22, or combinations thereof (H5 assay B). In some examples, the disclosed methods further include determining if an influenza virus is the Eurasian H7 subtype, by using the forward primer shown in SEQ ID NO: 23, the reverse primer shown in SEQ ID NO: 24, the probe shown in SEQ ID NO: 25, or combinations thereof. In some examples, the disclosed methods further include determining if an influenza virus is the North American H7 subtype, by using the forward primer shown in SEQ ID NO: 26, the reverse primer shown in SEQ ID NO: 27, the probe shown in SEQ ID NO: 28, or combinations thereof. In some examples, the disclosed methods further include determining if an influenza virus is the H9 subtype, by using the forward primer shown in SEQ ID NO: 29, the reverse primer shown in SEQ ID NO: 30, the probe shown in SEQ ID NO: 31, or combinations thereof.

Thus, in some examples, the disclosed kits include probes and/or primers for detecting an influenza H3 subtype, such as the forward primer shown in SEQ ID NO: 10, the reverse primer shown in SEQ ID NO: 11, the probe shown in SEQ ID NO: 12 and/or, or combinations thereof. In some examples, the disclosed kits include probes and/or primers for detecting an influenza H5 subtype, such as the forward primer shown in SEQ ID NO: 14 or 15, the reverse primer shown in SEQ ID NO: 16 or 17, the probe shown in SEQ ID NO 18 and/or 19, or combinations thereof (H5 assay A). In some examples, the disclosed kits include probes and/or primers for detecting an influenza H5 subtype, such as the forward primer shown in SEQ ID NO: 20, the reverse primer shown in SEQ ID NO: 21, the probe shown in SEQ ID NO: 22, or combinations thereof (H5 assay B). In some examples, the disclosed kits include probes and/or primers for detecting an influenza Eurasian H7 subtype, such as the forward primer shown in SEQ ID NO: 23, the reverse primer shown in SEQ ID NO: 24, the probe shown in SEQ ID NO: 25, or combinations thereof. In some examples, the disclosed kits include probes and/or primers for detecting an influenza North American H7 subtype, such as the forward primer shown in SEQ ID NO: 26, the reverse primer shown in SEQ ID NO: 27, the probe shown in SEQ ID NO: 28, or combinations thereof. In some examples, the disclosed kits include probes and/or primers for detecting an influenza H9 subtype, such as the forward primer shown in SEQ ID NO: 29, the reverse primer shown in SEQ ID NO: 30, the probe shown in SEQ ID NO: 31, or combinations thereof.

TABLE 1

Real-time PCR Primers and Probes

| Primer/Probe | Sequence (5' to 3') | SEQ ID NO: |
|---|---|---|
| H3 Universal Forward | GATCTYAAAAGCACTCARGCAGC | 10 |
| H3 Universal Reverse | AGGTCCTGAATTCTYCCTTCKAC | 11 |
| H3 Seasonal probe (Sea H3) | GATCTYAAAAGCACTCARGCAGCTCCCGA"T"CAA YCKATTCAGCTTCCCATTGA | 12 |
| H3 Variant probe (H3v) | TCTTGATTAC"T"CTRTTYAGTTTCCCGGTG | 13 |
| H5a Forward 1 | TGGAAAGTGTRAGAAACGGRACRTA | 14 |
| H5a Forward 2 | TGGAAAGTATAAGRAACGGAACRTA | 15 |

TABLE 1-continued

Real-time PCR Primers and Probes

| Primer/Probe | Sequence (5' to 3') | SEQ ID NO: |
|---|---|---|
| H5a Reverse 1 | CTAGGGARCTCGCCACTGTWGA | 16 |
| H5a Reverse 2 | CTAGDGAACTCGCARCTGTTGA | 17 |
| H5a Probe 1 | TGACTACCCGCAG"T"ATTCAGAAGAAKCAAGAYT AA | 18 |
| H5a Probe 2 | CAACTATCCGCAG"T"ATTCAGAAGAAGCAAGATT AA | 19 |
| H5b Forward | GGAATGYCCCAAATATGTGAAATCAA | 20 |
| H5b Reverse | CCRCTCCCCTGCTCRTTRCT | 21 |
| H5b Probe | TACCCA"T"ACCAACCATCTACCATYCCCTGCCAT | 22 |
| EuH7 Forward | AATGCACARGGRGAGGGAACTGC | 23 |
| EuH7 Reverse | CATTGCTACYAAGAGTTCAGCRTT | 24 |
| EuH7 Probe | ACCACACYTC"T"GTYATRGAATCTCTGGTCCA | 25 |
| NA H7 Forward | AAAYGCACAAGGAGARGGAACTGC | 26 |
| NA H7 Reverse | GCATTRTACGACCATAYCTCAGTCATT | 27 |
| NA H7 Probe | AAAGCACYCARTC"T"GCAATAGATCAGATCACAG G | 28 |
| H9 Forward | CTGGARTCTGARGGRACTTACAA | 29 |
| H9 Reverse | AARAAGGCAGCAAACCCCATTG | 30 |
| H9 Probe | CYATTTAT"T"CRACTGTCGCCTCATCTCTTG | 31 |
| FluB Forward | TCCTCAAYTC ACTCTTCGAGCG | 32 |
| FluB Reverse | CGGTGCTCTTGACCAAATTGG | 33 |
| FluB Probe | CCAATTCGAGCAGCTGAAACTGCGGTG | 34 |
| Rnase P Forward | AGATTTGGACCTGCGAGCG | 35 |
| Rnase P Reverse | GAGCGGCTGTCTCCACAAGT | 36 |
| Rnase P Probe | TTCTGACCTGAAGGCTCTGCGCG | 37 |

R = A + G; Y = C + T; K = G + T; W = A + T; D = G + A + T

EXAMPLES

The present disclosure is illustrated by the following non-limiting Examples.

Example 1

Materials and Methods

This example describes probes and primers and methods used for the detection, typing and subtyping of influenza virus.

Primer and probe sequences for real-time PCR are shown in Tables 1 and 2. The pdm H1 version 2 primer and probe sequences were designed to address aberrant reactivity due to point mutations in the original 2009 pdm H1 assay probe binding site, found in the HA gene of circulating strains of genetic clade 6B.1. Probes were labeled with 6-carboxyfluorescein (FAM) reporter molecule at the 5' end. A "BHQ® probe," as used herein, further comprised an internal Black Hole Quencher®-1 (BHQ® 1) at "T," and a spacer at the 3' end to prevent extension of the probe by Taq polymerase (for example, C3 Spacer, Integrated DNA Technologies, Inc., Coralville, Iowa, USA). Alternatively, where an internal "T" is not available at a useful location (such as in the InfA probe (SEQ ID NO: 6)), a BHQ® probe was prepared by attaching BHQ® 1 quencher molecule at the 3' end of the probe. A "ZEN™ probe," as used herein, was prepared by labeling the probe with FAM at the 5' end, an internal ZEN™ quencher located nine nucleotides from the 5' end, and an Iowa Black® FQ quencher (IABkFQ) at the 3' end. Additional useful labels, combinations of labels, and label positions are known to those of ordinary skill in the art.

TABLE 2

| Real-time PCR Primers and Probes | | |
|---|---|---|
| Primer/Probe* | Sequence (5' to 3') | SEQ ID NO: |
| pdm H1-Verision 2 Forward Primer | GTGCTATAAACACCAGCCTCCCATT | 1 |
| pdm H1-Verision 2 Reverse Primer | AGAYGGGACATTCCTCAATCCTG | 2 |
| pdm H1-Verision 2 Probe | ATACATCCRA"T"CACAATTGGRAAATGTCCAAA | 3 |
| Inf A Forward Primer | GACCRATCCTGTCACCTCTGAC | 4 |
| Inf A Reverse Primer | AGGGCATTYTGGACAAAKCGTCTA | 5 |
| Inf A Probe | TGCAGTCCTCGCTCACTGGGCACG | 6 |
| pdm Inf A Forward Primer | TTGCAGTAGCAAGTGGGCATGA | 7 |
| pdm Inf A Reverse Primer | TCTTGTGAGCTGGGTTTTCATTTG | 8 |
| pdm Inf A Probe | TGAATGGGTC"T"ATCCCGACCAGTGAGTAC | 9 |

*In the sequences R = A or G; Y = C or T; pdmH1-V2: influenza subtype H1 pandemic 2009-Version 2 primers and probes; Inf A: influenza type A primers and probes; Pdm Inf A: 2009 pandemic influenza type A primers and probes SEQ ID NOs: 1 and 4-9 are disclosed in PCT/US2014/0061802, SEQ ID NOs: 4-6 are also disclosed in Shu et al., *J. Clin. Microbiol.* 49:2614-2619, 2011, both of which disclosures are incorporated herein by reference in their entirety.

Hydrolysis probe (TAQMAN®) rRT-PCR reactions were performed using Invitrogen SuperScript® III Platinum® One-Step qRT-PCR kit (Life Technologies, Carlsbad, Calif.), or qScript™ One-Step qRT-PCR kit (Quanta Biosciences, Gaithersburg, Md.), according to the manufacturer's recommended procedures. Primer and probe reaction concentrations were 0.8 μM and 0.2 μM, respectively. Each reaction included 20 μl of rRT-PCR master mix. The master mix was prepared as shown in Table 3.

TABLE 3

| rRT-PCR Master Mix | | |
|---|---|---|
| | Invitrogen | Quanta |
| Nuclease free water | N × 5.5 μl | N × 5.5 μl |
| Forward primer (0.8 μM final concentration) | N × 0.5 μl | N × 0.5 μl |
| Reverse primer (0.8 μM final concentration) | N × 0.5 μl | N × 0.5 μl |
| Probe (0.2 μM final concentration) | N × 0.5 μl | N × 0.5 μl |
| RT Mix | N × 0.5 μl | N × 0.5 μl |
| 2X PCR Master Mix | N × 12.5 μl | N × 12.5 μl |
| Total volume | N × 20.0 μl | N × 20.0 μl |

N is the number of samples including non-template controls plus 1.

Twenty microliters of each master mix was added into individual wells of a 96 well plate. Then 5 μl of sample (or control) was added to each well. Prior to an rRT-PCR run, the 96 well plate was centrifuged at 500×g for 30 seconds at 4° C. The plate was loaded into a thermocycler and subjected to the PCR cycle conditions shown in Table 4.

TABLE 4

| rRT-PCR conditions | | |
|---|---|---|
| | Invitrogen | Quanta |
| Reverse Transcription | 50° C. for 30 min | 50° C. for 30 min |
| Taq inhibitor inactivation | 95° C. for 2 min | 95° C. for 5 min |
| PCR amplification (45 cycles) | 95° C. for 15 sec | 95° C. for 15 sec |
| | 55° C. for 30 sec* | 55° C. for 30 sec* |

*Fluorescence data was collected during the 55° C. incubation step.

rRT-PCR reactions were performed using Invitrogen SuperScript® III Platinum® One-Step qRT-PCR kit (Life Technologies, Carlsbad, Calif.) or qScript™ One-Step qRT-PCR kit (Quanta Biosciences, Gaithersburg, Md.), according to the manufacturer's recommended procedures. Primer and probe reaction concentrations were 0.8 μM and 0.2 respectively. Reactions were carried out in a 7500 Fast Dx Real-Time PCR instrument (Applied Biosystems, Foster City, Calif.) or an MX3005 QPCR system (Stratagene, La Jolla, Calif.) as shown in Table 2. The reaction volume was 25 μl.

Example 2

Detection of Influenza H1 Viruses by rRT-PCR

This example describes detection of influenza A H1 viruses by rRT-PCR assay.

rRT-PCR was performed as described in Example 1 using two influenza viruses: A/California/07/2009 (a 2009 pandemic influenza type A virus) and A/West Virginia/01/2016 (a recently emerged subtype H1 pandemic 2009 virus). The assay compared virus detection using a previously described influenza subtype H1 pandemic 2009 (pdm H1-Version 1 or pdmH1-V1) primers and probe set is disclosed in PCT/US2014/061802 and Centers for Disease Control and Prevention, "Seasonal Influenza Real-time rRT-PCR Panel Primer and Probe Sets," Jun. 8, 2012, which references are incorporated herein by reference in their entirety. The primers/probe set of SEQ ID NOs: 1, 2, and 3 (Table 2) is referred to herein as 2009 pandemic influenza subtype H1-Version 2 (pdm H1-V2).

Genetic reassortment between human and avian or swine influenza viruses can result in a novel virus with a hemagglutinin and/or neuraminidase against which humans lack immunity. The avian and swine influenza outbreaks of the early 21st century caused by H1N1pdm09, H5N1, H7N3, H7N7, H7N9, and H9N2 subtype influenza viruses, and their infection of humans, have created a new awareness of the pandemic potential of influenza viruses that circulate in domestic poultry and swine. Multiple infective subtypes and strains of 2009 pandemic influenza subtype H1 have emerged and continue to circulate in the population. Thus, there is a continuing need for tests that provide sensitive, specific detection of influenza types and subtypes in a relatively short time in order to permit rapid and effective treatment of an infected person. As shown in Table 5, the previous 2009 pandemic influenza subtype H1 specific (pdm H1-V1) assay did not detect influenza virus A/West Virginia/01/2016 at any concentration, while the influenza subtype H1 pandemic 2009 specific (pdm H1-V2) assay disclosed herein detected this virus using either the SuperScript® III or the Quant qScript™ qRT-PCR systems and using either BHQ® or ZEN™ quenchers.

TABLE 5

Detection of A/West Virginia/01/2016 comparing detection by pdm H1-V1 or pdm H1-V2 primers/probe sets in the assay

| Infectious Titer | Ct Value | | | | | | | | |
|---|---|---|---|---|---|---|---|---|---|
| ($EID_{50}$/ml) | pdmH1-V1 | | | pdmH1-V2(BHQ) | | | pdmH1-V2(ZEN) | | |
| Invitrogen SuperScript ® III 1-Step qRT-PCR system (N = 3) | | | | | | | | | |
| $10^{3.4}$ | — | — | — | 27.30 | 27.42 | 27.28 | 27.10 | 27.32 | 27.06 |
| $10^{2.4}$ | — | — | — | 30.96 | 31.12 | 30.15 | 30.50 | 30.68 | 31.00 |
| $10^{1.4}$ | — | — | — | 33.96 | 34.28 | 33.63 | 34.30 | 34.38 | 34.19 |
| $10^{0.4}$ | — | — | — | 37.87 | 37.09 | 37.22 | 36.22 | 36.20 | 36.22 |
| $10^{-0.6}$ | — | — | — | — | — | 38.30 | — | — | — |
| $10^{-1.6}$ | — | — | — | — | — | — | — | — | — |
| $10^{-2.6}$ | — | — | — | — | — | — | — | — | — |
| Quanta qScript ™ 1-Step qRT-PCR system (N = 3) | | | | | | | | | |
| $10^{3.4}$ | — | — | — | 27.41 | 27.31 | 27.28 | 26.96 | 26.88 | 26.85 |
| $10^{2.4}$ | — | — | — | 31.11 | 30.87 | 31.12 | 30.72 | 31.04 | 30.56 |
| $10^{1.4}$ | — | — | — | 33.75 | 34.26 | 34 | 34.17 | 33.99 | 33.89 |
| $10^{0.4}$ | — | — | — | 36.62 | 38.63 | 39.51 | — | 36.62 | 35.85 |
| $10^{-0.6}$ | — | — | — | — | — | — | — | 37.31 | 38.77 |
| $10^{-1.6}$ | — | — | — | — | — | — | — | 40.47 | 39.07 |
| $10^{-2.6}$ | — | — | — | — | — | — | 39.65 | — | — |

The A/California/07/2009 virus is a 2009 pandemic influenza type A virus that pre-dates the emergence of subtype H1 pandemic 2009 viruses. Detection of A/California/07/2009 virus was performed comparing detection with the pdm H1-Version 1 or pdm H1-Version 2 primers/probe sets in the assays. The use of BHQ® or ZEN™ probe quenchers was also compared. The result were generally comparable (Table 6). However, the pdm H1-V2 assay had slightly lower Ct values at each infectious titer than the pdm H1-Version 1 assay, particularly using the Quanta qScript™ qRT-PCR system.

TABLE 6

Detection of A/California/07/2009 comparing pdm H1-V1 or pdm H1-V2 primers/probe sets in the assay

| Infectious Titer | Ct Value | | | | | | | | |
|---|---|---|---|---|---|---|---|---|---|
| ($EID_{50}$/ml) | pdmH1-V1 | | | pdmH1-V2(BHQ) | | | pdmH1-V2(ZEN) | | |
| Invitrogen SuperScript ® III 1-Step qRT-PCR system (N = 3) | | | | | | | | | |
| $10^{6.5}$ | 25.23 | 25.31 | 25.22 | 25.19 | 25.19 | 25.29 | 24.45 | 24.5 | 24.37 |
| $10^{5.5}$ | 28.62 | 28.45 | 28.56 | 28.16 | 27.58 | 28.56 | 27.76 | 27.83 | 27.96 |
| $10^{4.5}$ | 31.76 | 31.63 | 31.75 | 31.76 | 31.68 | 32.02 | 31.2 | 31.14 | 31.56 |
| $10^{3.5}$ | 35.27 | 35.49 | 36.13 | 34.26 | 34.99 | 34.77 | 35.24 | 35.11 | 33.67 |
| $10^{2.5}$ | — | 40.60 | 38.39 | 36.80 | — | 37.33 | 36.72 | 38.12 | 36.98 |
| $10^{1.5}$ | — | — | — | 37.59 | — | — | — | — | — |
| $10^{0.5}$ | — | — | — | — | — | — | — | — | — |
| $10^{-0.5}$ | — | — | — | — | — | — | — | — | — |
| Quanta qScript ™ 1-Step qRT-PCR system (N = 3) | | | | | | | | | |
| $10^{6.5}$ | 25.71 | 25.09 | 25.51 | 24.85 | 24.39 | 23.61 | 22.56 | 23.26 | 22.55 |
| $10^{5.5}$ | 29.05 | 28.77 | 29.03 | 27.53 | 27.47 | 27.98 | 25.43 | 26.62 | 26.56 |
| $10^{4.5}$ | 32.45 | 32.26 | 32.39 | 31.38 | 31.28 | 31.49 | 29.47 | 30.01 | 29.5 |
| $10^{3.5}$ | 36.12 | 37.11 | 35.04 | 33.98 | 34.41 | 34.38 | 33.28 | 33.12 | 33.76 |
| $10^{2.5}$ | — | 38.12 | — | 35.9 | — | — | — | — | — |
| $10^{1.5}$ | — | 44.07 | — | 35.99 | — | — | — | 34.93 | 38.45 |
| $10^{0.5}$ | — | — | — | — | — | — | — | — | — |
| $10^{-0.5}$ | — | — | — | — | — | — | — | — | — |

TABLE 7

Comparison of the number of mismatched sequence positions within the pdmH1-V1 and pdmH1-V2 probe region to 2009 pandemic influenza A(H1N1) viruses
The mismatched number (and percentage of mismatches) between probed viral region and pdm H1 probe from 5,135 2009 pandemic influenza A(H1N1) viruses downloaded from GISAID from Jan. 1, 2016-Sep. 19, 2016

| | | Number of viral sequence (Percentage) with mismatches with probe region | | | | |
|---|---|---|---|---|---|---|
| | | 0 | 1 | 2 | 3 | 4 |
| pdm H1 Probe* | Version 1 (V1) | 514 (10.0%) | 3853 (75.0%) | 753 (14.7%) | 15 (0.3%) | 0 |
| pdm H1 Probe (SEQ ID NO: 3) | Version 2 (V2) | 4940 (96.2%) | 175 (3.4%) | 18 (0.3%) | 0 | 0 |

*Subtype H1 pandemic 2009 probe, Version 1 (pdm H1-Version 1), probe sequence was disclosed as SEQ ID NO: 33 in PCT/US2014/061802.
GISAID: Global Initiative on Sharing All Influenza Data.

The results of Table 7 indicate that the subtype H1 pandemic 2009 probe Version 2 (SEQ ID NO: 3) has fewer mismatches with the H1 pandemic 2009 probe region in recent, known influenza A (H1N1) pandemic 2009 viruses. Specifically, 3.4% and 0.3% of the viruses tested had zero or one mismatch, respectively. The Version 2 probe had zero mismatches in 96.2% of the H1 pandemic 2009 probe region. By contrast, the earlier disclosed subtype H1 pandemic 2009 probe (Version 1) showed 10.0% zero mismatches, 75.0% one mismatch, 14.7% two mismatches and 0.3% three mismatch. These results indicate that the pdm H1-V2 probe has improved sequence similarity with recently circulating H1 pandemic 2009 viruses. The results in this Table 7 are consistent with the results of Table 5 in which a known H1 pandemic 2009 virus (A/West Virginia/01/2016) was detected at by the pdmH1-Version 2 probe but not by the pdmH1-Version 1 probe.

Example 3

Detection of Influenza Viruses by rRT-PCR

This example describes detection of Influenza A viruses by rRT-PCR assay using the primers and probes described herein.

rRT-PCR was performed as described in Example 1 using two influenza viruses: A/California/07/2009 and A/West Virginia/01/2016. The assay utilized the previously described influenza type A (InfA) primer and probe set shown in Table 2 (SEQ ID NOS: 4, 5, and 6, see e.g., WO 2015/061475 and Shu et al., *J. Clin. Microbiol.* 49:2614-2619, 2011) and the previously described primer/probe set are referred to herein as pdm InfA (SEQ ID NOs: 7, 8, and 9).

Detection of A/West Virginia/01/2016 and A/California/07/2009 virus was performed using the InfA (primers/probe set comprising SEQ ID NOs: 4, 5, and 6, see Table 2) and pdm InfA (primers/probe set comprising SEQ ID NOS: 7, 8, and 9, see Table 2). Assays were generally comparable for two assay systems (compare results from Tables 8 and 9). The probe type is indicated as a ZEN™ probe or a BHQ® probe, which probe types are described herein.

TABLE 8

Detection of A/West Virginia/01/2016 and A/California/07/2009 with Invitrogen SuperScript ® III 1-Step qRT-PCR system

| Influenza Virus | Infectious Titer ($EID_{50}$/ml) | Ct Value InfA (ZEN ™) | | | pdmInfA (BHQ ®) | | | pdmInfA (ZEN ™) | | |
|---|---|---|---|---|---|---|---|---|---|---|
| A/West Virginia/01/2016 | | | | | | | | | | |
| | $10^{3.4}$ | 22.64 | 22.34 | 22.34 | 22.2 | 22.07 | 22.3 | 21.46 | 22.09 | 21.69 |
| | $10^{2.4}$ | 26.3 | 26.43 | 26.58 | 25.93 | 25.85 | 25.98 | 25.2 | 25.54 | 25.62 |
| | $10^{1.4}$ | 30.15 | 30.55 | 30.12 | 29.31 | 29.7 | 30.2 | 29.05 | 29.36 | 29.8 |
| | $10^{0.4}$ | 34.53 | 34.35 | 34.09 | 32.95 | 32.85 | 33.25 | 34.13 | 32.65 | 33.94 |
| | $10^{-0.6}$ | — | — | — | — | 34.76 | — | — | — | 34.32 |
| | $10^{-1.6}$ | — | — | — | — | — | — | — | — | — |
| | $10^{-2.6}$ | — | — | — | — | — | — | — | — | — |
| A/California/07/2009 | | | | | | | | | | |
| | $10^{6.5}$ | 22.06 | 21.46 | 21.62 | 21.06 | 20.69 | 20.89 | 20.87 | 20.62 | 20.79 |
| | $10^{5.5}$ | 25.23 | 25.31 | 25.14 | 24.28 | 24.37 | 24.36 | 24.34 | 24.26 | 24.37 |
| | $10^{4.5}$ | 28.65 | 29.11 | 28.35 | 27.71 | 27.75 | 27.92 | 28 | 28.1 | 27.23 |

TABLE 8-continued

Detection of A/West Virginia/01/2016 and A/California/07/2009 with Invitrogen SuperScript ® III 1-Step qRT-PCR system

| Influenza Virus | Infectious Titer ($EID_{50}$/ml) | Ct Value | | | | | | | | |
|---|---|---|---|---|---|---|---|---|---|---|
| | | InfA (ZEN ™) | | | pdmInfA (BHQ ®) | | | pdmInfA (ZEN ™) | | |
| | $10^{3.5}$ | 32.84 | 31.72 | 31.78 | 31.04 | 31.17 | 31.04 | 31.72 | 31.23 | 31.8 |
| | $10^{2.5}$ | 33.9 | 38.23 | 35.37 | 33.58 | — | 33.52 | 35.04 | 36.08 | 35.85 |
| | $10^{1.5}$ | — | — | — | — | — | — | — | 36.03 | — |
| | $10^{0.5}$ | — | — | — | — | — | — | — | — | — |
| | $10^{-0.5}$ | — | — | — | — | — | — | — | — | — |

TABLE 9

Detection of A/West Virginia/01/2016 and A/California/07/2009 with Quanta qScript ™ 1-Step qRT-PCR system (N = 3)

| Influenza Virus | Infectious Titer ($EID_{50}$/ml) | Ct Value | | | | | | | | |
|---|---|---|---|---|---|---|---|---|---|---|
| | | InfA (ZEN ™) | | | pdmInfA (BHQ ®) | | | pdmInfA (ZEN ™) | | |
| A/West Virginia/01/2016 | | | | | | | | | | |
| | $10^{3.4}$ | 22.02 | 22.09 | 21.9 | 23.19 | 23.09 | 23.5 | 22.48 | 22.35 | 22.45 |
| | $10^{2.4}$ | 26.2 | 25.41 | 26.66 | 27.08 | 27.16 | 27.18 | 26.31 | 26.43 | 26.43 |
| | $10^{1.4}$ | 29.39 | 29.88 | 29.59 | 31.34 | 31.75 | 31.22 | 30.13 | 29.75 | 30.42 |
| | $10^{0.4}$ | 34.12 | 33.15 | 32.73 | 33.98 | 36.09 | 34.79 | 33.02 | 33.57 | 35.07 |
| | $10^{-0.6}$ | 36.51 | — | — | 36.65 | 36.14 | — | — | 35.49 | — |
| | $10^{-1.6}$ | — | 35.16 | — | — | — | — | — | — | — |
| | $10^{-2.6}$ | — | — | — | — | — | — | — | — | — |
| A/California/07/2009 | | | | | | | | | | |
| | $10^{6.5}$ | 19.96 | 20.2 | 20.06 | 21.1 | 21.15 | 21.3 | 20.5 | 20.6 | 20.48 |
| | $10^{5.5}$ | 24.14 | 23.87 | 23.43 | 24.87 | 24.46 | 24.7 | 24.27 | 23.57 | 23.6 |
| | $10^{4.5}$ | 27.36 | 27.17 | 27.14 | 28 | 28.4 | 28.2 | 27.62 | 27.04 | 27.5 |
| | $10^{3.5}$ | 30.59 | 30.75 | 30.59 | 31.21 | 32.01 | 32.31 | 30.6 | 30.42 | 30.88 |
| | $10^{2.5}$ | — | 34.04 | 35.11 | — | 34.4 | 34.86 | 36.4 | — | 35.48 |
| | $10^{1.5}$ | — | — | — | — | — | — | — | — | 34.93 |
| | $10^{0.5}$ | — | — | — | — | — | — | — | — | — |
| | $10^{-0.5}$ | — | — | — | — | — | — | — | — | — |

Example 4

Analytical Sensitivity—Limit of Detection Study (LOD)

Analytical sensitivity of the pdm H1 assays was demonstrated by determining the approximate limit of detection (LOD, range-finding study, n=3 per each analyte concentration) using Quanta qScript™ and Invitrogen SuperScript® III enzyme kits using pdm H1-V1 and pdm H1-V2 primers/probe sets and assayed according to the protocols of Example 1, herein. The viruses tested were the historic virus A/California/07/2009 and the more recently emerged virus A/West Virginia/01/2016. The latter strain includes point mutations that cause aberrant results with the pdm H1-V1 assay. Characterized viruses of known 50% infectious dose titers ($ID_{50}$/mL) were extracted, and the RNA was serially diluted and tested (n=3 replicates) in order to determine an estimated LOD (the lowest concentration at which 3 of 3 replicates are detected). These studies were conducted with Invitrogen Superscript® and Quanta qscript™.

The results of the range-finding LOD study indicate equivalent reactivity between the prior pdm H1-V1 assay and the pdm H1-V2 assay for the historic virus A/California/07/2009. The results for A/West Virginia/01/2016 confirm that the pdm H1-V2 assay detects the virus bearing the point mutation that was not detected by the pdm H1-V1 assay.

The estimated LOD for each primers/probe set was confirmed by testing extraction replicates (n=20) of the highest virus dilution where ≥95% of all replicates tested positive. Virus dilutions were prepared in virus transport medium containing human A549 cells to emulate clinical specimen matrix. The lowest concentration where the InfA, pdmInfA, and pdmH1-V2 primer and probe sets demonstrated uniform detection was reported as the LOD. The results are summarized in the Table 10.

TABLE 10 pdmH1-V2 Assay LOD Results

| Influenza Virus Tested | Influenza Strain Designation | LOD ($ID_{50}$/mL) Invitrogen SuperScript ® | LOD ($ID_{50}$/mL) Quanta qScript ™ |
|---|---|---|---|
| A(H1)pdm09 | A/West Virginia/01/2016 | $10^{0.9}$ | $10^{0.9}$ |
| | A/California/07/2009 | $10^{3.1}$ | $10^{3.8}$ |

A comparison study was conducted to demonstrate LOD equivalency for the A/H3 assays between the currently cleared BHQ®-1 and ZEN™ assays. RNA was extracted from A/Hong Kong/4801/2014 virus, serially diluted, and three replicates per dilution were tested. The results indicated similar analytical sensitivity between the assays with ZEN™ double quencher or BHQ®-1 quencher attached to the probes.

Example 5

Analytical Performance: Analytical Inclusivity

An inclusivity study was conducted to demonstrate the capability of the modified primers/probe rRT-PCR mixtures (pdmH1-V2, InfA, and pdmInfA (SEQ ID NOs: 1 to 9 (see Table 2) with ZEN™ quencher (an influenza A subtyping kit) to detect influenza A(H1)pdm09 viruses representative of different geographic locations and phylogenetic clades. It is understood that a subtyping kit, intended to detect influenza A 2009 pandemic H1 virus or other emerging viruses, includes the pdmH1-V2 primers/probe set and may further include additional primers/probe sets as described herein.

Inclusivity testing was performed with ten representative H1pdm09 viruses at or near the established LOD. The viruses were grown to high titer, harvested, and serially diluted to near the LOD of the assays. The diluted viruses were extracted and tested (n=3 replicates) to demonstrate reactivity.

An influenza A subtyping kit (comprising or consisting of the pdm H1-V2 primers/probe set (SEQ ID NOs: 1, 2, and 3), the InfA primers/probe set (SEQ ID NOs: 4, 5, and 6), and the pdmInfA primers/probe set (SEQ ID NOs: 6, 7, and 8) was reactive with all H1pdm09 virus isolates tested. The inclusivity results are presented in Table 11.

TABLE 11

Identification of Influenza Virus Strains using an influenza A subtyping kit (comprising primers/probe sets InfA, pdmInfA, and pdmH1-V2).

| Influenza virus strain 2009 pandemic | LOD | Invitrogen SuperScript ™ | | | Quanta qScript ™ | | |
|---|---|---|---|---|---|---|---|
| influenza A(H1N1) virus identification | ($ID_{50}$/mL) | InfA | pdm InfA | pdmH1 ver2 | InfA | pdm InfA | pdmH1 ver2 |
| A/California/04/2009 | $10^{2.9}$ | 3/3 (+) | 3/3 (+) | 3/3 (+) | 3/3 (+) | 3/3 (+) | 3/3 (+) |
| A/California/07/2009 | $10^{3.5}$ | 3/3 (+) | 3/3 (+) | 3/3 (+) | 3/3 (+) | 3/3 (+) | 3/3 (+) |
| A/Colorado/14/2012 | $10^{1.1}$ | 3/3 (+) | 3/3 (+) | 3/3 (+) | 3/3 (+) | 3/3 (+) | 3/3 (+) |
| A/Florida/27/2011 | $10^{1.9}$ | 3/3 (+) | 3/3 (+) | 3/3 (+) | 3/3 (+) | 3/3 (+) | 3/3 (+) |
| A/Florida/62/2014 | $10^{2.2}$ | 3/3 (+) | 3/3 (+) | 3/3 (+) | 3/3 (+) | 3/3 (+) | 3/3 (+) |
| A/Maryland/13/2012 | $10^{1.0}$ | 3/3 (+) | 3/3 (+) | 3/3 (+) | 3/3 (+) | 3/3 (+) | 3/3 (+) |
| A/Minnesota/03/2011 | $10^{3.9}$ | 3/3 (+) | 3/3 (+) | 3/3 (+) | 3/3 (+) | 3/3 (+) | 3/3 (+) |
| A/North Carolina/4/2014 | $10^{3.3}$ | 3/3 (+) | 3/3 (+) | 3/3 (+) | 3/3 (+) | 3/3 (+) | 3/3 (+) |
| A/Utah/13/2016 | $10^{1.5}$ | 3/3 (+) | 3/3 (+) | 3/3 (+) | 3/3 (+) | 3/3 (+) | 3/3 (+) |
| A/Washington/24/2012 | $10^{2.5}$ | 3/3 (+) | 3/3 (+) | 3/3 (+) | 3/3 (+) | 3/3 (+) | 3/3 (+) |

Example 6

Analytical Performance: Cross-Reactivity

Cross-reactivity of an influenza A subtyping kit (comprising primers/probe sets for 2009 pandemic influenza subtype H1 version 2 (pdmH1-V2, SEQ ID NOs: 1, 2, and 3), influenza A (InfA, SEQ ID NOS: 4, 5, and 6), and 2009 pandemic influenza A (pdmInfA, SEQ ID NOS: 7, 8, and 9) was evaluated for the ability to detect variant viruses by testing influenza A(H1) virus strains representing diverse geographic locations and different sources. Samples were tested in triplicate using RNA extracted from high titer preparations of viruses (≥$10^6$ $EID_{50}$/mL). Cross-reactivity testing of the influenza A subtyping kit, comprising InfA, pdmInfA, and pdmH1-V2 primers/probe sets, was evaluated using two enzyme systems (i.e., Invitrogen SuperScrip® III and Quanta qScript™). Extraction was performed according to the protocol of Example 1, herein.

As shown in Table 12, all of the viruses were positive for influenza A detection but not all of the viruses tested positive as 2009 pandemic influenza A or 2009 pandemic influenza subtype H1. The reactivity data for four influenza A(H1) variant (A(H1v)) viruses, A/Iowa/1/2006, A/Texas/14/2008, A/Ohio/09/2015, and A/Minnesota/19/2011 were included in the cross reactivity table. The data in Table 12 demonstrate that the pandemic primers/probe sets, pdmInfA and pdmH1-V2 do not detect human seasonal A(H1N1) viruses (such as A/Brisbane/59/07 and A/Hawaii/15/2001), as expected. However, the pdmInfA and pdmH1-V2 primers/probe sets detected variant influenza viruses. Variant influenza viruses (such as, for example, H1N1v, H1N2v and H3N2v variant influenza viruses) normally circulate in swine and occasionally infect humans. The pdmInfA primers/probe set hybridizes to the NP gene and the pdmH1-V2 primers/probe set hybridizes to the HA gene segments of these influenza variant viruses because these variants contain a high level of similarity with 2009 A(H1N1) pandemic virus. These data show that the 2009 pandemic primers/probe set (InfA/pdmInfA/pdmH1-V2) is useful to detect emerging non-human, variant influenza viruses so as to reduce the risk for continued transmission.

TABLE 12

Influenza Viruses Tested for Cross-Reactivity using InfA, pdm InfA and pdm H1-V2 primers/probe sets

| | | | Average Ct (triplicate) | | | | | |
|---|---|---|---|---|---|---|---|---|
| | | | Invitrogen SuperScript ™ | | | Quanta qScript ™ | | |
| Strain Designation | Subtype | $ID_{50}$/mL | InfA | pdm InfA | pdm H1-V2 | InfA | pdm InfA | pdm H1-V2 |
| A/Brisbane/59/07 | A(H1N1) | $10^{8.4}$ | 13.9 | — | — | 12.87 | — | — |
| A/Hawaii/15/2001 | A(H1N1) | $10^{8.1}$ | 15.18 | — | — | 14.72 | — | — |
| A/Iowa/1/2006 | A(H1N1v) | $10^{8.2}$ | 15.03 | 15.07 | 25.65 | 15.28 | 15.13 | 28.43 |
| A/Texas/14/2008 | A(H1N1v) | $10^{8.3}$ | 16.32 | 17.03 | 28.74 | 14.1 | 14.71 | 27.24 |
| A/Ohio/09/2015 | A(H1N1v) | $10^{7.7}$ | 13.63 | 13.77 | 15 | 15.11 | 16.1 | 19.36 |
| A/Minnesota/19/2011 | A(H1N2v) | $10^{7.1}$ | 15.31 | 17.39 | — | 15.26 | 20.24 | — |

Example 7

Clinical Performance Evaluation

The clinical performance of oligonucleotide primer and probe sets of the influenza A subtyping kit disclosed herein (using pdmH1-V2 (version 2) primers/probe sets comprising SEQ ID NOS: 1, 2, and 3, for detection of emerging pandemic H1 viruses, and further comprising the InfA primers/probe set comprising SEQ ID NOs: 4, 5, and 6, and further comprising pdmInfA primers/probe set comprising SEQ ID NOs: 7, 8, and 9) were evaluated as positive or negative using archived clinical samples collected during the 2011-2012, 2013-2014, and 2015-2016 influenza seasons.

Clinical samples from forty-two specimens from the 2015-2016 influenza season produced aberrant results with the previously disclosed pdmH1-V1 (pdm H1 Version 1) assay. The sequences for the pdmH1-V1 primers and probe set are disclosed in PCT/US2014/061802. The clinical samples were confirmed to contain influenza subtype H1 pandemic 2009 virus (A(H1)pdm09) by genetic sequence analysis. These specimens were also tested to validate reactivity with the pdmH1-V2 primers/probe set (comprising primers/probe SEQ ID NOs: 1, 2, and 3, see Table 2). The assay results are shown in Table 13.

TABLE 13

Retrospective Positive Clinical Study Results - (H1)pdm09 Comparison

| | Invitrogen SuperScript ® III | | Quanta qScript ™ | |
|---|---|---|---|---|
| Specimen Type* | # of Positives | % Positive Agreement (95% CI) | # of Positives | % Positive Agreement (95% CI) |
| BW | 1/1 | 100.0 (20.7-100.0) | 1/1 | 100.0 (20.7-100.0) |
| NPS, NS | 34/35 | 97.1 (85.5-99.5) | 33/33 | 100.0 (89.6-100.0) |
| NW | 4/4 | 100.0 (51.0-100.0) | 4/4 | 100.0 (51.0-100.0) |
| TS | 2/2 | 100.00 (34.2-100.0) | 2/2 | 100.00 (34.2-100.0) |

*Specimens: bronchial wash (BW), nasopharyngeal swabs (NPS), nasal swabs (NS), nasal wash (NW), and throat swabs (TS)

The results in Table 13 indicate that samples, confirmed to contain subtype H1 pandemic 2009 (A(H1)pdm09) virus by genetic analysis, also tested positive for influenza A(H1) pdm09 using the InfA, pdmInfA, and pdmH1-V2 primers/probe sets. Forty-two clinical samples that were previously determined to be negative for 2009 pandemic influenza A(H1) virus (using the prior pdmH1-version 1 assay) were evaluated with the influenza A subtyping kit comprising InfA, pdmInfA, and pdmH1-V2 primers/probe sets (see Table 14). Samples that yielded inconclusive results were excluded from the analysis.

TABLE 14

Retrospective Negative Clinical Study Results - A(H1)pdm09

| | Invitrogen SuperScript ® III ® | | Quanta qScript ™ | |
|---|---|---|---|---|
| Specimen Type | # of Negatives[1] | % Negative Agreement (95% CI) | # of Negatives[1] | % Negative Agreement (95% CI) |
| NPS | 53/53 | 100.00 (93.2-100.0) | 52/52 | 100.00 (93.1-100.0) |

[1]Proportion of negative samples correctly identified versus the comparator.
Specimen: nasopharyngeal (NPS)

The results in Table 14 indicate that samples previously shown to be negative for influenza virus A(H1)pdm09 using the prior pdmH1-V1 primers/probe set, also tested negative using the pdmH1-V2 primers/probe set, thereby confirming the specificity of the pdmH1-V2 primers/probe set.

The pandemic H1-Version 2 primers/probe set (SEQ ID NOs: 1, 2, and 3), demonstrate the need for a modified pdm H1 assay and the usefulness of the pdm H1-V2 primers, probe and assays disclosed herein, thereby ensuring comprehensive detection of influenza A(H1)pdm09 virus subtypes and emerging pdm H1 subtypes and strains. Analytical and clinical data demonstrate that the performance of the methods, primers, probes, kits, and devices provided herein detect 2009 pandemic influenza A subtype H1 (A(H1) pdm09) viruses and pandemic influenza subtype H1 viruses emerging subsequent to the 2009 pandemic.

Example 8

Clinical Performance and Reproducibility

Forty-one A(H1N1)pdm09 positive and fifty-three negative respiratory specimens collected from human patients with influenza-like illness were evaluated to demonstrate clinical performance. Performance of the pdmH1 ver2 assay showed 100% agreement when compared to genetic sequence analysis (Table 15).

TABLE 15

| Clinical performance of pdmH1 ver2 assay | | | | |
|---|---|---|---|---|
| | Comparator Method pdmH1 rRTPCR & Genetic Sequencing Analysis (Sanger) | | | |
| | A(H1N1)pdm09 Positive | A(H1N1)pdm09 Negative | Total | Performance |
| A(H1N1)pdm09 Positive | 41 | 0 | 41 | 100% Sensitivity |
| A(H1N1)pdm09 Negative | 0 | 53 | 53 | 100% Specificity |
| Total | 43 | 53 | 94 | |

Six A(H1N1)pdm09 positive and negative samples were tested by two qualified technicians on two separate days to demonstrate reproducibility (Table 16).

TABLE 16

| Reproducibility results summary | | | | | | | | |
|---|---|---|---|---|---|---|---|---|
| | InfA | | pdmInfA | | pdmH1 ver 2 | | RP | |
| | Agreement w/expected | Avg. Ct | Agreement w/expected | Avg. Ct | Agreement w/expected | Avg. Ct | Agreement w/expected | Avg. Ct |
| Sample 1 | 6/6 | 18.45 | 6/6 | 18.35 | 6/6 | 20.83 | 6/6 | 25.92 |
| Sample 2 | 6/6 | 0 | 6/6 | 0 | 6/6 | 0 | 6/6 | 25.21 |
| Sample 3 | 6/6 | 21.4 | 6/6 | 21.21 | 6/6 | 22.89 | 6/6 | 25.52 |
| Sample 4 | 6/6 | 18.2 | 6/6 | 18.18 | 6/6 | 20.62 | 6/6 | 25.65 |
| Sample 5 | 6/6 | 0 | 6/6 | 0 | 6/6 | 0 | 6/6 | 25.1 |
| Sample 6 | 6/6 | 21.22 | 6/6 | 21.09 | 6/6 | 23.43 | 6/6 | 25.43 |
| HSC | — | — | — | — | — | — | — | 28.21 |
| Positive Control | 6/6 | + | 6/6 | + | 6/6 | + | 6/6 | + |

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A kit for detecting an influenza virus nucleic acid molecule in a sample, comprising: a probe consisting of the nucleic acid sequence of SEQ ID NO: 3 and at least one detectable label attached to the probe, wherein the detectable label comprises a radioactive isotope, enzyme substrate, co-factor, ligand, chemiluminescent agent, fluorophore, fluorescence quencher, hapten, enzyme, chemical, or combinations thereof; and a forward primer consisting of SEQ ID NO: 1; and a reverse primer consisting of SEQ ID NO: 2.

2. The kit of claim 1, further comprising:

(a) a detectably labeled probe comprising SEQ ID NO: 6; a forward primer comprising SEQ ID NO: 4; and a reverse primer comprising SEQ ID NO: 5; and/or (b) a detectably labeled probe comprising SEQ ID NO: 9; a forward primer comprising SEQ ID NO: 7; and a reverse primer comprising SEQ ID NO: 8.

3. The kit of claim 1, further comprising:

a probe comprising of SEQ ID NO: 12;

a probe comprising of SEQ ID NO: 13;

nucleic acid primers comprising SEQ ID NO: 10 and SEQ ID NO: 11;

nucleic acid primers comprising SEQ ID NO: 14 and SEQ ID NO: 15;

nucleic acid primers comprising SEQ ID NO: 16 and SEQ ID NO: 17;

a probe comprising SEQ ID NO: 18;

a probe comprising SEQ ID NO: 19;

nucleic acid primers comprising SEQ ID NO: 20 ad SEQ ID NO: 21;

a probe comprising SEQ ID NO: 22;

nucleic acid primers comprising SEQ ID NO: 23 and SEQ ID NO: 24;

a probe comprising SEQ ID NO: 25;

nucleic acid primers comprising SEQ ID NO: 26 and SEQ ID NO: 27;

a probe comprising SEQ ID NO: 28;

nucleic acid primers comprising SEQ ID NO: 29 and SEQ ID NO: 30;

a probe comprising SEQ ID NO: 31;

nucleic acid primers comprising SEQ ID NO: 32 and SEQ ID NO: 33;

a probe comprising SEQ ID NO: 34; or combinations thereof.

4. The kit of claim 1, further comprising a human RNAse P control probe.

5. The kit of claim 1 further comprising (a) a detectably labeled probe consisting of SEQ ID NO: 6;

forward primer consisting of SEQ ID NO: 4; and reverse primer consisting of SEQ ID NO: 5; and/or (b) a detectably labeled probe consisting of SEQ ID NO: 9;

a forward primer consisting of SEQ ID NO: 7; and a reverse primer consisting of SEQ ID NO: 8.

6. The kit of claim 1 further comprising a probe consisting of SEQ ID NO: 12;

a probe consisting of SEQ ID NO: 13;

nucleic acid primers consisting of SEQ ID NO: 10 and SEQ ID NO: 11;

nucleic acid primers consisting of SEQ ID NO: 14 and SEQ ID NO: 15;

nucleic acid primers consisting of SEQ ID NO: 16 and SEQ ID NO: 17;

a probe consisting of SEQ ID NO: 18;

a probe consisting of SEQ ID NO: 19;

nucleic acid primers consisting of SEQ ID NO: 20 and SEQ ID NO: 21;

a probe consisting of SEQ ID NO: 22;

nucleic acid primers consisting of SEQ ID NO: 23 and SEQ ID NO: 24;

a probe consisting of SEQ ID NO: 25;

nucleic acid primers consisting of SEQ ID NO: 26 and SEQ ID NO: 27;

a probe consisting of SEQ ID NO: 28;

nucleic acid primers consisting of SEQ ID NO: 29 and SEQ ID NO: 30;

a probe consisting of SEQ ID NO: 31;

nucleic acid primers consisting of SEQ ID NO: 32 and SEQ ID NO: 33;

a probe consisting of SEQ ID NO: 34; or combinations thereof.

7. A method for detecting an influenza virus nucleic acid molecule in a sample, comprising:

contacting nucleic acid from the sample with the probe and primers of the kit of claim 1;

amplifying the nucleic acid molecule by polymerase chain reaction (PCR), real-time PCR, reverse transcriptase-PCR, real-time reverse transcriptase-PCR, ligase chain reaction, or transcription-mediated amplification; and detecting hybridization between the detectably labeled probe and the influenza virus nucleic acid molecule, wherein detection of hybridization indicates an influenza virus nucleic acid molecule is present in the sample.

8. The method of claim 7, wherein the influenza virus is influenza virus A subtype H1 pandemic 2009.

9. The method of claim 7, further comprising:

contacting the sample with a detectably labeled nucleic acid probe comprising SEQ ID NO: 6 or a detectably labeled nucleic acid probe comprising SEQ ID NO: 9; and detecting hybridization between the detectably labeled probe comprising SEQ ID NO: 6 or the detectably labeled probe comprising SEQ ID NO: 9 and the influenza virus nucleic acid molecule, wherein detection of hybridization indicates presence of an influenza type A nucleic acid molecule in the sample.

10. The method of claim 9, further comprising contacting the sample with nucleic acid primers comprising SEQ ID NO: 4 and SEQ ID NO: 5 or with nucleic acid primers comprising SEQ ID NO: 7 and SEQ ID NO: 8.

11. The method of claim 7, wherein detecting hybridization comprises detecting a change in signal from the detectably labeled nucleic acid probe during or after hybridization relative to signal from the label before hybridization or wherein detecting hybridization between the detectably labeled nucleic acid probe and a nucleic acid molecule comprises performing real-time PCR, quantitative real-time PCR, or real time reverse transcriptase PCR.

12. The method of claim 7, wherein the probe is labeled with a fluorophore and/or a fluorescence quencher.

13. The method of claim 7, wherein the sample comprises an isolated virus; or the sample is a biological sample from a subject suspected of virus infection; or the sample comprises blood, derivatives of blood, fractions of blood, serum, extracted galls, biopsied or surgically removed tissue, unfixed tissue, frozen tissue, formalin-fixed tissue, paraffin-embedded tissue, autopsy sample, tears, milk, skin scrapes, surface washings, urine, sputum, cerebrospinal fluid, prostate fluid, pus, bone marrow aspirates, middle ear fluids, tracheal aspirates, nasopharyngeal aspirates or swabs, nasal swabs, nasal washes, throat swabs, dual nasopharyngeal/throat swabs, lower respiratory tract specimens, bronchoalveolar lavage, bronchial wash, sputum, lung tissue, oropharyngeal aspirates or swabs, saliva, or viral culture; or the sample is an environmental or food sample suspected of virus contamination.

14. The method of claim 7, further comprising contacting the sample with:

a probe comprising SEQ ID NO: 12;

a probe comprising SEQ ID NO: 13;

nucleic acid primers comprising SEQ ID NO: 10 and SEQ ID NO: 11;

nucleic acid primers comprising SEQ ID NO: 14 and SEQ ID NO: 15;

nucleic acid primers comprising SEQ ID NO: 16 and SEQ ID NO: 17;

a probe comprising SEQ ID NO: 18;

a probe comprising SEQ ID NO: 19;

nucleic acid primers comprising SEQ ID NO: 20 and SEQ ID NO: 21;

a probe comprising SEQ ID NO: 22;

nucleic acid primers comprising SEQ ID NO: 23 and SEQ ID NO: 24;

a probe comprising SEQ ID NO: 25;

nucleic acid primers comprising SEQ ID NO: 26 and SEQ ID NO: 27;

a probe comprising SEQ ID NO: 28;

nucleic acid primers comprising SEQ ID NO: 29 and SEQ ID NO: 30;

a probe comprising SEQ ID NO: 31;

nucleic acid primers comprising SEQ ID NO: 32 and SEQ ID NO: 33;

a probe comprising SEQ ID NO: 34; or combinations thereof.

15. The method of claim 7 further comprising:

contacting the sample with a detectably labeled nucleic acid probe consisting of SEQ ID NO: 6 or a detectably labeled nucleic acid probe consisting of SEQ ID NO: 9; and detecting hybridization between the detectably labeled probe consisting of SEQ ID NO: 6 or the detectably labeled probe consisting of SEQ ID NO: 9 and the influenza virus nucleic acid molecule, wherein detection of hybridization indicates presence of an influenza type A nucleic acid molecule in the sample.

16. The method of claim 15, further comprising contacting the sample with nucleic acid primers consisting of SEQ ID NO: 4 and SEQ ID NO: 5 or with nucleic acid primers consisting of SEQ ID NO: 7 and SEQ ID NO: 8.

17. The method of claim 7, further comprising contacting the sample with:

a probe consisting of SEQ ID NO: 12;

a probe consisting of SEQ ID NO: 13;

nucleic acid primers consisting of SEQ ID NO: 10 and SEQ ID NO: 11;

nucleic acid primers consisting of SEQ ID NO: 14 and SEQ ID NO: 15;

nucleic acid primers consisting of SEQ ID NO: 16 and SEQ ID NO: 17;

a probe consisting of SEQ ID NO: 18;

a probe consisting of SEQ ID NO: 19;

nucleic acid primers consisting of SEQ ID NO: 20 and SEQ ID NO: 21;

a probe consisting of SEQ ID NO: 22;

nucleic acid primers consisting of SEQ ID NO: 23 and SEQ ID NO: 24;

a probe consisting of SEQ ID NO: 25;

nucleic acid primers consisting of SEQ ID NO: 26 and SEQ ID NO: 27;

a probe consisting of SEQ ID NO: 28;

nucleic acid primers consisting of SEQ ID NO: 29 and SEQ ID NO: 30;

a probe consisting of SEQ ID NO: 31;

nucleic acid primers consisting of SEQ ID NO: 32 and SEQ ID NO: 33;

a probe consisting of SEQ ID NO: 34; or combinations thereof.

* * * * *